US008192988B2

(12) United States Patent
Sugaya et al.

(10) Patent No.: US 8,192,988 B2
(45) Date of Patent: Jun. 5, 2012

(54) METHODS FOR INCREASING POTENCY OF ADULT MESENCHYMAL STEM CELLS

(75) Inventors: Kiminobu Sugaya, Winter Park, FL (US); Angel Alvarez, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 1017 days.

(21) Appl. No.: 11/258,401

(22) Filed: Oct. 24, 2005

(65) Prior Publication Data

US 2006/0188489 A1     Aug. 24, 2006

Related U.S. Application Data

(60) Provisional application No. 60/621,901, filed on Oct. 22, 2004, provisional application No. 60/650,438, filed on Feb. 4, 2005.

(51) Int. Cl.
*C12N 15/00* (2006.01)
*C12N 5/00* (2006.01)
*C12N 5/02* (2006.01)

(52) U.S. Cl. ...................... 435/455; 435/320.1; 435/325
(58) Field of Classification Search ........................ None
See application file for complete search history.

(56) References Cited

U.S. PATENT DOCUMENTS

| 6,833,269 | B2 * | 12/2004 | Carpenter ...................... 435/377 |
| 7,618,621 | B2 | 11/2009 | Sugaya et al. |
| 7,635,467 | B2 | 12/2009 | Sugaya et al. |
| 2006/0110440 | A1 | 5/2006 | Sugaya et al. |
| 2006/0134789 | A1 | 6/2006 | Sugaya et al. |
| 2006/0188489 | A1 | 8/2006 | Sugaya et al. |

FOREIGN PATENT DOCUMENTS

| WO | WO 03/064463 A2 | 8/2003 |
| WO | WO 03064463 A2 * | 8/2003 |
| WO | WO 2004/072226 A2 | 8/2004 |
| WO | WO 2004072226 A2 * | 8/2004 |

OTHER PUBLICATIONS

Takahashi et al. (2006) Cell 126:663-676.*
Yu et al. (2007) Science 318:1917-1920.*
Richards (1997) Cell Mol Life Sci 53:790-802.*
Weissman (2000) Science 287:1442-1446.*
Mattson (2001) Expert Rev. Neurotherapeutics 1:267-273.*
Isacson (2003) Lancet Neurol 2:417-424.*
Lindvall et al. (2004) Nature Med 10 Suppl:S42-S50.*
Snyder et al. (2004) J Neurosci 76:157-168.*
Sugaya et al. (2006) Panminerva Med. 48:87-96.*
"The Human Embryonic Stem Cell and the Human Embryonic Germ Cell" Stem Cells: Scientific Progress and Future Research Directions. Department of Health and Human Services. Jun. 2001., http://stemcells.nih.gov/info/scireport/2001report, downloaded Feb. 8, 2008.*
Liu, et al. (Jul. 2004), Xi Bau Yu Fen Zi Mian Yi Xue Za Zhi, 20(4): 495-98 (Abstract Only).*
Mitsui, et al. (May 30, 2003) Cell, 113(5): 631-42.*
Hart, et al. (2004) Developmental Dynamics, 230: 187-98.*
Ma, et al. (2008) "G9a and Jhdm2a Regulate Embryonic Stem Cell Fusion-Induced Reprogramming of Adult Neural Stem Cells", Stem Cells, 26: 2131-41.*
Wang, et al. (Apr. 2008) "Requirement of Nanog Dimerization for Stem Cell Self-Renewal and Pluripotency", Proceedings of the National Academy of Science, U.S.A., 105(17): 6326-31.*
Theunissen, et al. (Jan. 2011) "Nanog Overcomes Reprogramming Barriers and Induces Pluripotency in Minimal Conditions", Current Biology, 21(1): 65-71.*
Silva, et al. (2009) "Nanog is the Gateway to the Pluripotent Ground State", Cell, 138: 722-37.*
Go, et al. (2008) "Forced Expression of Sox2 or Nanog in Human Bone Marrow Derived Mesenchymal Stem Cells Maintains Their Expansion and Differentiation Capabilities", Experimental Cell Research, 314(5): 1147-54 (Abstract Only).*
Liu, et al. (2009) "Effects of Ectopic Nanog and Oct4 Overexpression on Mesenchymal Stem Cells", Stem Cells and Development, 18(7): 1013-22 (Abstract Only).*
Okano, et al. (2009) "Strategies Toward CNS-Regeneration Using Induced Pluripotent Stem Cells", Genome Information, 23(1): 217-20 (Abstract Only).*
Patel, et al. (2010) "Advances in Reprogramming Somatic Stem Cells to Induced Pluripotent Stem Cells", Stem Cell Reviews, 6(3): 367-80.*
Pierantozzi, et al. (2011) "Pluripotency Regulators in Human Mesenchymal Stem Cells: Expression of NANOG but not of OCT-4 and SOX-2", Stem Cells and Development, 20(5): 915-23 (Abstract Only).*
Silva, et al. (2006) "Nanog Promotes Transfer of Pluripotency After Cell Fusion", Nature, 441(7096): 997-1001 (Abstract Only).*
Sumer, et al. (2011) "NANOG is a Key Factor for Induction of Pluripotency in Bovine Adult Fibroblasts", Journal of Animal Science, 441: 997-1001 (Absract Only).*
Zhao, et al. (2010) "Rapid and Efficient Reprogramming of Human Amnion-Derived Cells into Pluripotency by Three Factors OCT4/SOX2/\NANOG", Differentiation, 80(2-3): 123-29 (Abstract Only).*
Hatano, Shin-ya et al., "Pluripotential competence of cells associated with Nanog activity", Mechanisms of Development, 2005, vol. 122, pp. 67-79.
Silva, Jose et al., "Nanog promotes transfer of pluripotency after cell fusion", Nature, Jun. 22, 2006, vol. 44, pp. 997-1001, Nature Publishing Group.
Hart, Adam H. et al., "Identification, Cloning and Expression Analysis of the Pluripotency Promoting Nanog Genes in Mouse and Human", Developmental Dynamics, 2004, vol. 230, pp. 187-198.
Yu, Junying et al., "Induced Pluripotent Stem Cell Lines Derived from Human Somatic Cells", Science, 2007; 318, 1917, doi:10.1126/science.1151526.
Takahashi, Kazutoshi et al., "Induction of Pluripotent Stem Cells form Mouse Embryonic and Adult Fibroblast Cultures by Defined Factors", Cell, Aug. 25, 2006, vol. 126, pp. 663-676.

* cited by examiner

*Primary Examiner* — Robert M Kelly
(74) *Attorney, Agent, or Firm* — Timothy H. Van Dyke; Beusse, Wolter, Sanks, Mora & Maire, P.A.

(57) ABSTRACT

Disclosed herein are methods and materials for producing a more developmentally potent cell from a less developmentally potent cell. Specifically exemplified herein are methods that comprise introducing an expressible dedifferentiating polynucleotide sequence into a less developmentally potent cell, wherein the transfected less developmentally potent cell becomes a more developmentally potent cell capable of differentiating to a less developmentally potent cell of its lineage of origin or a different lineage.

5 Claims, 18 Drawing Sheets

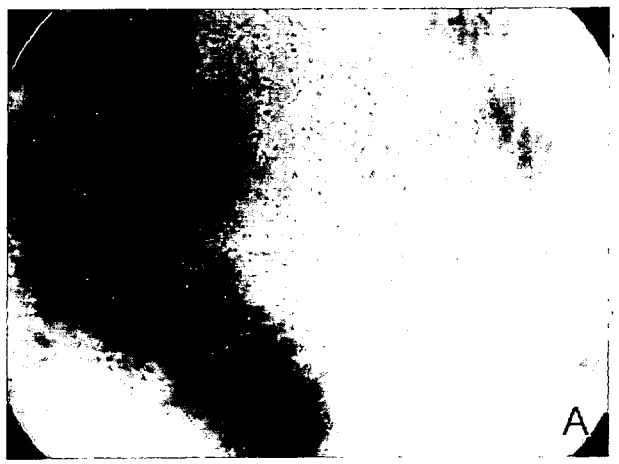
FIG. 5
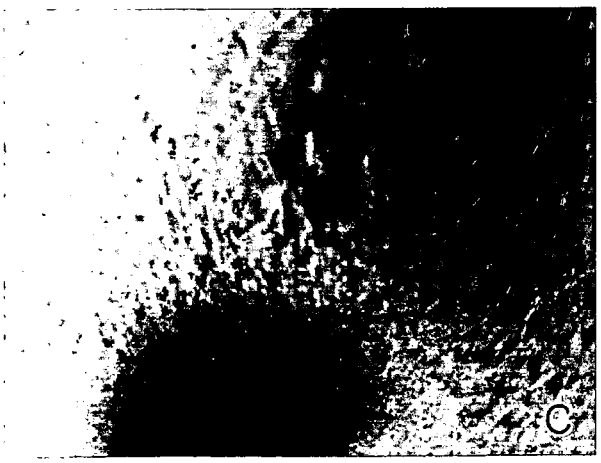

Green: βIII-tubulin, Red: GFAP, Blue: DAPI

Green: βIII-tubulin, Red: GFAP, Blue: DAPI

Green: βIII-tubulin, Red: GFAP, Blue: DAPI

FIG. 9: NanogP8 Sequence

```
t?tteetceteettcetc?atactaac
atgagtgtggatccagcttgtccccaaagcttgccttgctttgaagaatccgactgtaaa
 M  S  V  D  P  A  C  P  Q  S  L  P  C  F  E  E  S  D  C  K
gaatcttcacctatgcctgtgatttgtgggcctgaagaaaactatccatccttgcaaatg
 E  S  S  P  M  P  V  I  C  G  P  E  E  N  Y  P  S  L  Q  M
tcttctgctgagatgcctcacacagagactgtctctcctcttccttcctccatggatctg
 S  S  A  E  M  P  H  T  E  T  V  S  P  L  P  S  S  M  D  L
cttattcaggacagccctgattcttccaccagtcccaaaggcaaacaacccacttctgca
 L  I  Q  D  S  P  D  S  S  T  S  P  K  G  K  Q  P  T  S  A
gagaatagtgtcgcaaaaaaggaagacaaggtcccggtcaagaaacagaagaccagaact
 E  N  S  V  A  K  K  E  D  K  V  P  V  K  Q  K  T  R  T
gtgttctcttccacccagctgtgtgtactcaatgatagatttcagagacagaaatacctc
 V  F  S  S  T  Q  L  C  V  L  N  D  R  F  Q  R  Q  K  Y  L
agcctccagcagatgcaagaactctccaacatcctgaacctcagctacaaacaggtgaag
 S  L  Q  Q  M  Q  E  L  S  N  I  L  N  L  S  Y  K  Q  V  K
acctggttccagaaccagagaatgaaatctaagaggtggcagaaaaacaactggccgaag
 T  W  F  Q  N  Q  R  M  K  S  K  R  W  Q  K  N  N  W  P  K
aatagcaatggtgtgacgcagaaggcctcagcacctacctaccccagcctctactcttcc
 N  S  N  G  V  T  Q  K  A  S  A  P  T  Y  P  S  L  Y  S  S
taccaccagggatgcctggtgaacccgactgggaaccttccaatgtggagcaaccagacc
 Y  H  Q  G  C  L  V  N  P  T  G  N  L  P  M  ?  S  N  Q  T
tggaacaattcaacctggagcaaccagacccagaacatccagtcctggagcaaccactcc
 ?  N  N  S  T  ?  S  N  Q  T  Q  N  I  Q  S  ?  S  N  H  S
tggaacactcagacctggtgcacccaatcctggaacaatcaggcctggaacagtcccttc
 ?  N  T  Q  T  ?  C  T  Q  S  ?  N  N  Q  A  ?  N  S  P  F
tataactgtggagaggaatctctgcagtcctgcatgcacttccagccaaattctcctgcc
 Y  N  C  G  E  E  S  L  Q  S  C  M  H  F  Q  P  N  S  P  A
agtgacttggaggctgccttggaagctgctggggaaggccttaatgtaatacagcagacc
 S  D  L  E  A  A  L  E  A  A  G  E  G  L  N  V  I  Q  Q  T
actaggtatttagtactccacaaaccatggatttattcctaaactactccatgaacatg
 T  R  Y  F  S  T  P  Q  T  M  D  L  F  L  N  Y  S  M  N  M
caacctgaagacgtgtga
 Q  P  E  D  V  -
agatgagtgaaactgatattactcaatttcagtctggacactggctgaatccttcctct
                                                            c
ccctcctcccatccctcataggattttttcttgtttggaaaccacgtgttctggtttcca
                                                            t
``` gatgcctatccagtcaatctcatggagggtggagtatggttggagcctaatcagcgaggt
ttctttttttttttttcctattggatcttcctggagaaaatactttttttttttttttg
agacggagtcttgctctgtcgcccaggctggagtgcagtggcgcggtcttggctcactgc
aagctccgcctcccgggttcacgccattctcctgcctcagcctcccgagcagctgggact
acaggcgccgccacctcgcccggctaatattttgtattttagtagagacagggtttca
ctgtgttagccaggatggtctcgatctcctgaccttgtgatccgcccgcctcggcctccc
taacagctgggattacaggcgtgagccaccgcgccctgcctagaaaagacatttta ataa
ccttggctgctaaggacaacattgatagaagccgtctctggctatagataagtagatcta
atactagtttggatatctttagggtttagaatctaacctcaagaataagaaatacaagta
cgaattggtgatgaagatgtatt FIG. 9: NanogP8 Sequence (CONTINUED)

Electrophoresis 050115
Troponin I and hANP

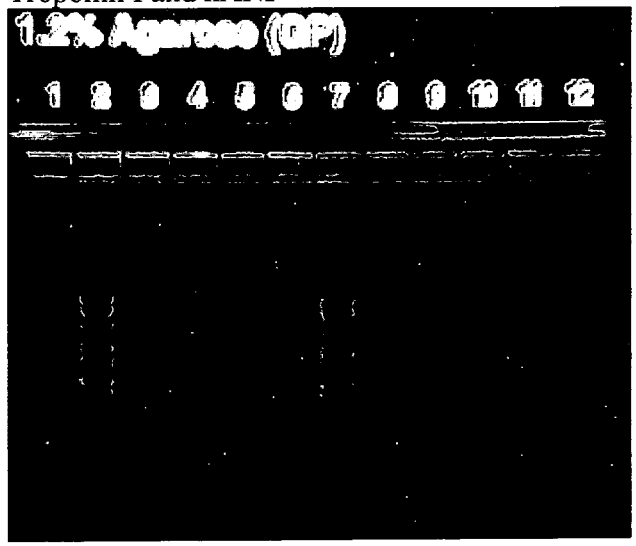

FIG. 11

GATA-4 and MLC-2v

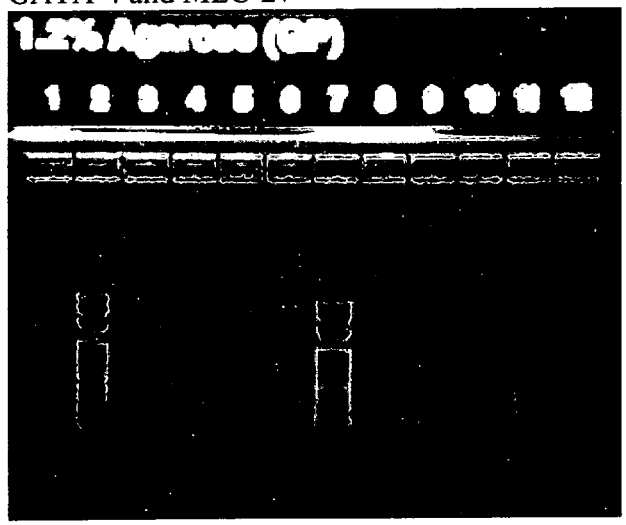

3 weeks of treatment (3uM BrdU or 5-azaC) and coculture for 7 days

Lane 2: ladder
Lane 3: Troponin I or GATA-4 low RNA of BrdU treatment
Lane 4: Troponin I or GATA-4 high RNA of BrdU treatment
Lane 5: Troponin I or GATA-4 low RNA of 5azaC treatment
Lane 6: Troponin I or GATA-4 high RNA of 5azaC treatment
Lane 7: ladder
Lane 8: hANP or MLC-2v low RNA of BrdU treatment
Lane 9: hANP or MLC-2v high RNA of BrdU treatment
Lane 10: hANP or MLC-2v low RNA of 5azaC treatment
Lane 11: hANP or MLC-2v high RNA of 5azaC treatment Electrophoresis 050116
Troponin I and hANP
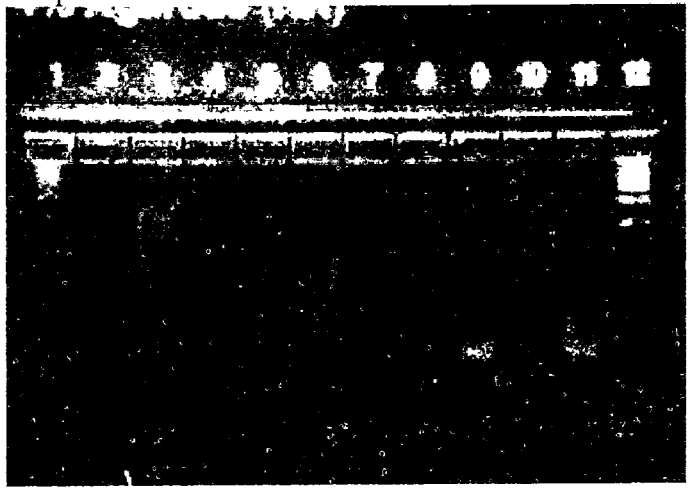
FIG. 12
GATA-4 and MLC-2v
Lane 1: 100bp ladder
Lane 2: 3uM combined treatment 3 weeks
Lane 3: 1uM combined treatment 3 weeks
Lane 4: 3uM 5azaC 3 weeks
Lane 5: 3uM BrdU 3 weeks
Lane 6: 3uM Control (nt 12/27)
Lane 7: 3uM combined treatment 3 weeks
Lane 8: 1uM combined treatment 3 weeks
Lane 9: 3uM 5azaC 3 weeks
Lane 10: 3uM BrdU 3 weeks
Lane 11: 3uM Control (nt 12/27)
Lane 12: 100bp ladder GATA-4 and MLC-2v
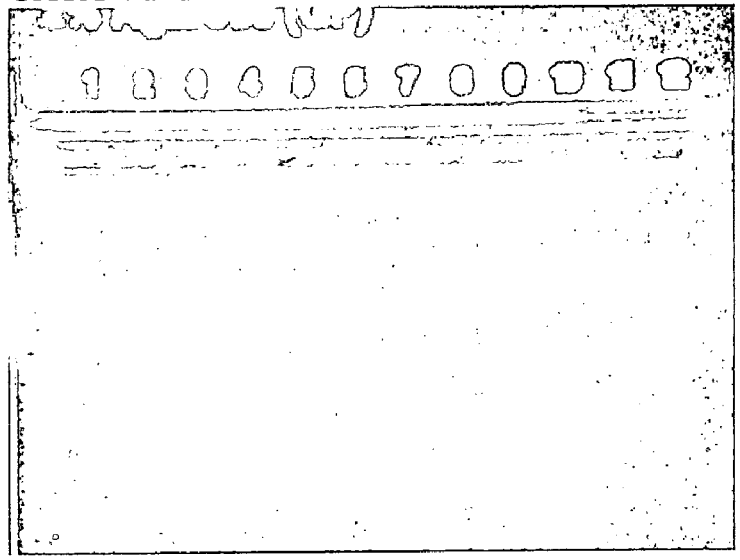
FIG. 13
Troponin I and hANP
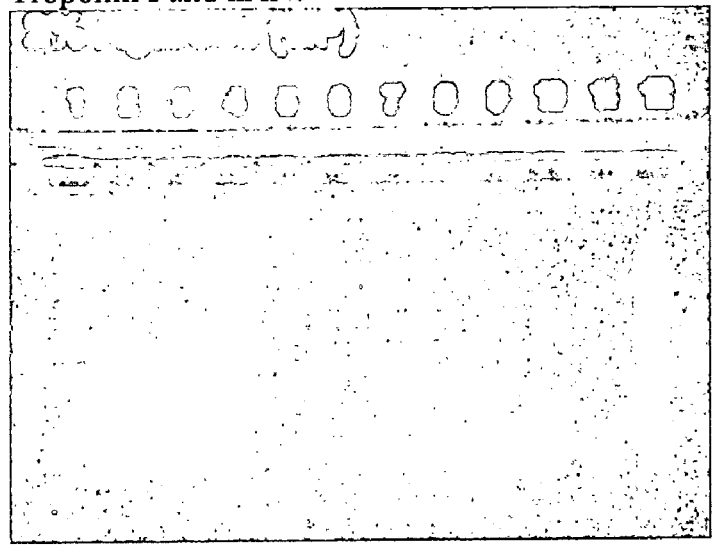
Lane 1: DNA ladder
Lane 2: 10uM 5azaC treatment
Lane 3: 3uM 5azaC treatment
Lane 4: 1uM 5azaC treatment
Lane 5: 3uM 5azaC treatment
Lane 6: 3uM BrdU treatment
Lane 7: 10uM 5azaC treatment
Lane 8: 3uM 5azaC treatment
Lane 9: 1uM 5azaC treatment
Lane 10: 3uM 5azaC treatment
Lane 11: 3uM BrdU treatment
Lane 12: DNA ladder

Nanog vector sequence analysis

SEQUENCE LISTING

```
<160> NUMBER OF SEQ ID NOS: 9

<210> SEQ ID NO 1
<211> LENGTH: 1628
<212> TYPE: DNA
<213> ORGANISM: Homo sapiens
<220> FEATURE:
<221> NAME/KEY: CDS
<222> LOCATION: (28)..(945)

<400> SEQUENCE: 1
tttttcctcc tcttcctcta tactaac atg agt gtg gat cca gct tgt ccc caa      54
                                Met Ser Val Asp Pro Ala Cys Pro Gln
                                 1               5 agc ttg cct tgc ttt gaa gaa tcc gac tgt aaa gaa tct tca cct atg      102
Ser Leu Pro Cys Phe Glu Glu Ser Asp Cys Lys Glu Ser Ser Pro Met
 10              15                  20                  25 cct gtg att tgt ggg cct gaa gaa aac tat cca tcc ttg caa atg tct      150
Pro Val Ile Cys Gly Pro Glu Glu Asn Tyr Pro Ser Leu Gln Met Ser
                30                  35                  40 tct gct gag atg cct cac aca gag act gtc tct cct ctt cct tcc tcc      198
Ser Ala Glu Met Pro His Thr Glu Thr Val Ser Pro Leu Pro Ser Ser
            45                  50                  55 atg gat ctg ctt att cag gac agc cct gat tct tcc acc agt ccc aaa      246
Met Asp Leu Leu Ile Gln Asp Ser Pro Asp Ser Ser Thr Ser Pro Lys
        60                  65                  70 ggc aaa caa ccc act tct gca gag aat agt gtc gca aaa aag gaa gac      294
Gly Lys Gln Pro Thr Ser Ala Glu Asn Ser Val Ala Lys Lys Glu Asp
 75                  80                  85
```

| | |
|---|---|
| aag gtc ccg gtc aag aaa cag aag acc aga act gtg ttc tct tcc acc<br>Lys Val Pro Val Lys Lys Gln Lys Thr Arg Thr Val Phe Ser Ser Thr<br>90                        95                    100                      105 | 342 |
| cag ctg tgt gta ctc aat gat aga ttt cag aga cag aaa tac ctc agc<br>Gln Leu Cys Val Leu Asn Asp Arg Phe Gln Arg Gln Lys Tyr Leu Ser<br>                    110                      115                    120 | 390 |
| ctc cag cag atg caa gaa ctc tcc aac atc ctg aac ctc agc tac aaa<br>Leu Gln Gln Met Gln Glu Leu Ser Asn Ile Leu Asn Leu Ser Tyr Lys<br>                125                      130                    135 | 438 |
| cag gtg aag acc tgg ttc cag aac cag aga atg aaa tct aag agg tgg<br>Gln Val Lys Thr Trp Phe Gln Asn Gln Arg Met Lys Ser Lys Arg Trp<br>140                        145                    150 | 486 |
| cag aaa aac aac tgg ccg aag aat agc aat ggt gtg acg cag aag gcc<br>Gln Lys Asn Asn Trp Pro Lys Asn Ser Asn Gly Val Thr Gln Lys Ala<br>     155                    160                    165 | 534 |
| tca gca cct acc tac ccc agc ctc tac tct tcc tac cac cag gga tgc<br>Ser Ala Pro Thr Tyr Pro Ser Leu Tyr Ser Ser Tyr His Gln Gly Cys<br>170                        175                    180                    185 | 582 |
| ctg gtg aac ccg act ggg aac ctt cca atg tgg agc aac cag acc tgg<br>Leu Val Asn Pro Thr Gly Asn Leu Pro Met Trp Ser Asn Gln Thr Trp<br>                    190                      195                    200 | 630 |
| aac aat tca acc tgg agc aac cag acc cag aac atc cag tcc tgg agc<br>Asn Asn Ser Thr Trp Ser Asn Gln Thr Gln Asn Ile Gln Ser Trp Ser<br>                205                      210                    215 | 678 |
| aac cac tcc tgg aac act cag acc tgg tgc acc caa tcc tgg aac aat<br>Asn His Ser Trp Asn Thr Gln Thr Trp Cys Thr Gln Ser Trp Asn Asn<br>     220                    225                    230 | 726 |
| cag gcc tgg aac agt ccc ttc tat aac tgt gga gag gaa tct ctg cag<br>Gln Ala Trp Asn Ser Pro Phe Tyr Asn Cys Gly Glu Glu Ser Leu Gln<br>    235                    240                    245 | 774 |
| tcc tgc atg cac ttc cag cca aat tct cct gcc agt gac ttg gag gct<br>Ser Cys Met His Phe Gln Pro Asn Ser Pro Ala Ser Asp Leu Glu Ala<br>250                        255                    260                    265 | 822 |
| gcc ttg gaa gct gct ggg gaa ggc ctt aat gta ata cag cag acc act<br>Ala Leu Glu Ala Ala Gly Glu Gly Leu Asn Val Ile Gln Gln Thr Thr<br>                    270                      275                    280 | 870 |
| agg tat ttt agt act cca caa acc atg gat tta ttc cta aac tac tcc<br>Arg Tyr Phe Ser Thr Pro Gln Thr Met Asp Leu Phe Leu Asn Tyr Ser<br>                285                      290                    295 | 918 |
| atg aac atg caa cct gaa gac gtg tga agatgagtga aactgatatt<br>Met Asn Met Gln Pro Glu Asp Val<br>300                        305 | 965 |
| actcaatttc agtctggaca ctggctgaat ccttcctctc ccctcctccc atccctcata | 1025 |
| ggatttttct tgtttggaaa ccacgtgttc tggtttccat gatgcctatc cagtcaatct | 1085 |
| catggagggt ggagtatggt tggagcctaa tcagcgaggt ttcttttttt tttttttccta | 1145 |
| ttggatcttc ctggagaaaa tactttttt tttttttttg agacggagtc ttgctctgtc | 1205 |
| gcccaggctg gagtgcagtg gcgcggtctt ggctcactgc aagctccgcc tcccgggttc | 1265 |
| acgccattct cctgcctcag cctcccgagc agctgggact acaggcgccc gccacctcgc | 1325 |
| ccggctaata ttttgtattt ttagtagaga caggggtttca ctgtgttagc caggatggtc | 1385 |
| tcgatctcct gaccttgtga tccgcccgcc tcggcctccc taacagctgg gattacaggc | 1445 |
| gtgagccacc gcgccctgcc tagaaaagac attttaataa ccttggctgc taaggacaac | 1505 |
| attgatagaa gccgtctctg gctatagata agtagatcta atactagttt ggatatcttt | 1565 |
| agggtttaga atctaacctc aagaataaga aatacaagta cgaattggtg atgaagatgt | 1625 |
| att | 1628 |

```
<210> SEQ ID NO 2
<211> LENGTH: 305
<212> TYPE: PRT
<213> ORGANISM: Homo sapiens

<400> SEQUENCE: 2

Met Ser Val Asp Pro Ala Cys Pro Gln Ser Leu Pro Cys Phe Glu Glu
 1               5                  10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Asn Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met His Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttttcctcc tcttcctcta                                              20
```

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
attggtgatg aagatgtatt                                                 20

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6 His Tag

<400> SEQUENCE: 5

His His His His His His
  1               5

<210> SEQ ID NO 6
<211> LENGTH: 1417
<212> TYPE: DNA
<213> ORGANISM: Homo sapiens

<400> SEQUENCE: 4
```

| | | | | | |
|---|---|---|---|---|---|
| tcccttcgca | agccctcatt | tcaccaggcc | cccggcttgg | ggcgccttcc | ttccccatgg    60 |
| cgggacacct | ggcttcggat | ttcgccttct | cgcccctcc  | aggtggtgga | ggtgatgggc   120 |
| caggggggcc | ggagccgggc | tgggttgatc | ctcggacctg | gctaagcttc | caaggccctc   180 |
| ctggagggcc | aggaatcggg | ccggggggttg | ggccaggctc | tgaggtgtgg | gggattcccc   240 |
| catgcccccc | gccgtatgag | ttctgtgggg | ggatggcgta | ctgtgggccc | caggttggag   300 |
| tggggctagt | gccccaaggc | ggcttggaga | cctctcagcc | tgagggcgaa | gcaggagtcg   360 |
| gggtggagag | caactccgat | ggggcctccc | cggagccctg | caccgtcacc | cctggtgccg   420 |
| tgaagctgga | gaaggagaag | ctggagcaaa | acccggagga | gtcccaggac | atcaaagctc   480 |
| tgcagaaaga | actcgagcaa | tttgccaagc | tcctgaagca | aagaggatc | ccctgggat    540 |
| atacacaggc | cgatgtgggg | ctcacccctg | gggttctatt | tgggaaggta | ttcagccaaa   600 |
| cgaccatctg | ccgctttgag | gctctgcagc | ttagcttcaa | gaacatgtgt | aagctgcggc   660 |
| ccttgctgca | gaagtgggtg | gaggaagctg | acaacaatga | aaatcttcag | gagatatgca   720 |
| aagcagaaac | cctcgtgcag | gcccgaaaga | gaaagcgaac | cagtatcgag | aaccgagtga   780 |
| gaggcaacct | ggagaatttg | ttcctgcagt | gcccgaaacc | cacactgcag | cagatcagcc   840 |
| acatcgccca | gcagcttggg | ctcgagaagg | atgtggtccg | agtgtggttc | tgtaaccggc   900 |
| gccagaaggg | caagcgatca | agcagcgact | atgcacaacg | agaggatttt | gaggctgctg   960 |
| ggtctccttt | ctcagggggga | ccagtgtcct | ttcctctggc | cccagggccc | cattttggta  1020 |
| ccccaggcta | tgggagccct | cacttcactg | cactgtactc | ctcggtccct | ttccctgagg  1080 |
| gggaagcctt | tccccctgtc | tccgtcacca | ctctgggctc | tccatgcat  | tcaaactgag  1140 |
| gtgcctgccc | ttctaggaat | ggggacagg  | ggaggggag  | gagctaggga | aagaaaacct  1200 |
| ggagtttgtg | ccagggtttt | tgggattaag | ttcttcattc | actaaggaag | gaattgggaa  1260 |
| cacaaagggt | gggggcaggg | gagtttgggg | caactggttg | gagggaaggt | gaagttcaat  1320 |

```
gatgctcttg attttaatcc cacatcatgt atcactttt tcttaaataa agaagcctgg    1380
gacacagtaa aaaaaaaaaa aaaaaaaaaa aaaaaa                             1417
```

<210> SEQ ID NO 7
<211> LENGTH: 360
<212> TYPE: PRT
<213> ORGANISM: Homo sapiens

<400> SEQUENCE: 7

```
Met Ala Gly His Leu Ala Ser Asp Phe Ala Phe Ser Pro Pro Pro Gly
 1               5                  10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360
```

<210> SEQ ID NO 8
<211> LENGTH: 2518
<212> TYPE: DNA
<213> ORGANISM: Homo sapiens

<400> SEQUENCE: 8

| | | | | | |
|---|---|---|---|---|---|
| ctattaactt | gttcaaaaaa | gtatcaggag | ttgtcaaggc | agagaagaga | gtgtttgcaa | 60 |
| aaggggaaa | gtagtttgct | gcctctttaa | gactaggact | gagagaaaga | agaggagaga | 120 |
| gaaagaaagg | gagagaagtt | tgagccccag | gcttaagcct | ttccaaaaaa | taataataac | 180 |
| aatcatcggc | ggcggcagga | tcggccagag | gaggagggaa | gcgcttttt | tgatcctgat | 240 |
| tccagtttgc | ctctctcttt | ttttccccca | aattattctt | cgcctgattt | tcctcgcgga | 300 |
| gccctgcgct | cccgacaccc | ccgcccgcct | cccctcctcc | tctcccccg | cccgcgggcc | 360 |
| ccccaaagtc | ccggccgggc | cgagggtcgg | cggccgccgg | cgggccgggc | ccgcgcacag | 420 |
| cgcccgcatg | tacaacatga | tggagacgga | gctgaagccg | ccgggcccgc | agcaaacttc | 480 |
| ggggggcggc | ggcggcaact | ccaccgcggc | ggcggccggc | ggcaaccaga | aaaacagccc | 540 |
| ggaccgcgtc | aagcggccca | tgaatgcctt | catggtgtgg | tcccgcgggc | agcggcgcaa | 600 |
| gatggcccag | gagaacccca | agatgcacaa | ctcggagatc | agcaagcgcc | tgggcgccga | 660 |
| gtggaaactt | ttgtcggaga | cggagaagcg | gccgttcatc | gacgaggcta | agcggctgcg | 720 |
| agcgctgcac | atgaaggagc | acccggatta | taaataccgg | ccccggcgga | aaaccaagac | 780 |
| gctcatgaag | aaggataagt | acacgctgcc | cggcgggctg | ctggccccg | gcggcaatag | 840 |
| catggcgagc | ggggtcgggg | tgggcgccgg | cctgggcgcg | ggcgtgaacc | agcgcatgga | 900 |
| cagttacgcg | cacatgaacg | gctggagcaa | cggcagctac | agcatgatgc | aggaccagct | 960 |
| gggctacccg | cagcacccgg | gcctcaatgc | gcacggcgca | gcgcagatgc | agcccatgca | 1020 |
| ccgctacgac | gtgagcgccc | tgcagtacaa | ctccatgacc | agctcgcaga | cctacatgaa | 1080 |
| cggctcgccc | acctacagca | tgtcctactc | gcagcagggc | acccctggca | tggctcttgg | 1140 |
| ctccatgggt | tcggtggtca | agtccgaggc | cagctccagc | cccctgtgg | ttacctcttc | 1200 |
| ctcccactcc | agggcgccct | gccaggccgg | ggacctccgg | gacatgatca | gcatgtatct | 1260 |
| ccccggcgcc | gaggtgccgg | aacccgccgc | ccccagcaga | cttcacatgt | cccagcacta | 1320 |
| ccagagcggc | ccggtgcccg | gcacggccat | taacggcaca | ctgccctct | cacacatgtg | 1380 |
| agggccggac | agcgaactgg | agggggaga | aattttcaaa | gaaaaacgag | ggaaatggga | 1440 |
| ggggtgcaaa | agaggagagt | aagaaacagc | atggagaaaa | cccggtacgc | tcaaaaagaa | 1500 |
| aaggaaaaa | aaaaaatccc | atcacccaca | gcaaatgaca | gctgcaaaag | agaacaccaa | 1560 |
| tcccatccac | actcacgcaa | aaccgcgat | gccgacaaga | aaactttat | gagagagatc | 1620 |
| ctggacttct | tttggggga | ctattttgt | acagagaaaa | cctggggagg | gtggggaggg | 1680 |
| cgggggaatg | gaccttgtat | agatctggag | gaaagaaagc | tacgaaaaac | ttttaaaag | 1740 |
| ttctagtggt | acggtaggag | ctttgcagga | agtttgcaaa | agtctttacc | aataatattt | 1800 |
| agagctagtc | tccaagcgac | gaaaaaaatg | ttttaatatt | tgcaagcaac | ttttgtacag | 1860 |
| tatttatcga | gataaacatg | gcaatcaaaa | tgtccattgt | ttataagctg | agaatttgcc | 1920 |
| aatattttc | aaggagaggc | ttcttgctga | attttgattc | tgcagctgaa | atttaggaca | 1980 |
| gttgcaaacg | tgaaagaag | aaaattattc | aaatttggac | attttaattg | tttaaaaatt | 2040 |
| gtacaaaagg | aaaaaattag | aataagtact | ggcgaaccat | ctctgtggtc | ttgtttaaaa | 2100 |
| agggcaaaag | ttttagactg | tactaaattt | tataacttac | tgttaaaagc | aaaaatggcc | 2160 |
| atgcaggttg | acaccgttgg | taatttataa | tagcttttgt | tcgatcccaa | ctttccattt | 2220 |

```
tgttcagata aaaaaaacca tgaaattact gtgtttgaaa tatttcttta tggtttgtaa    2280
tatttctgta aatttattgt gatattttaa ggttttcccc cctttatttt ccgtagttgt    2340
attttaaaag attcggctct gtattatttg aatcagtctg ccgagaatcc atgtatatat    2400
ttgaactaat atcatcctta taacaggtac attttcaact taagttttta ctccattatg    2460
cacagtttga gataaataaa ttttttgaaat atggacactg aaaaaaaaaa aaaaaaa     2518
```

<210> SEQ ID NO 9
<211> LENGTH: 317
<212> TYPE: PRT
<213> ORGANISM: Homo sapiens

<400> SEQUENCE: 9

```
Met Tyr Asn Met Met Glu Thr Glu Leu Lys Pro Pro Gly Pro Gln Gln
 1               5                  10                  15

Thr Ser Gly Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315
```

METHODS FOR INCREASING POTENCY OF ADULT MESENCHYMAL STEM CELLS

CROSS-REFERENCE TO RELATED APPLICATIONS

This application claims priority to U.S. Ser. No. 60/621,901 filed Oct. 22, 2004 and 60/650,438 filed Feb. 4, 2005, both of which are incorporated herein in their entirety

BACKGROUND OF THE INVENTION

The use of stem cells for the treatment of neurodegenerative conditions offers the hope of curing diseases like Alzheimer's and Parkinson's by means of transplantation [1]. However, major obstacles regarding cell procurement, directing cell fate and avoiding immune response hinder clinical development [2-4] Research has focused on both adult and embryonic stem cells and attempted to balance limitations in regulating their development and preventing immune response. Increased potency of stem cells can be achieved by epigenetic modifications through nucleotide derivatives [5] and their lineage can be directed by gene transfection [6,7].

Patients currently suffering from neurodegenerative conditions have limited treatment options. Conventional drug therapy helps delay or reduce the symptoms of disease but is unable to restore complete functionality of the brain or repair damaged tissue. Through stem cell-based therapies, scientists aim to transplant cells in order to regenerate damaged tissue and restore proper function. However, the best source of stem cells for transplantation remains an unresolved issue; with debate focusing around embryonic or adult derived stem cells. Embryonic stem cells can be readily differentiated to multiple neuronal fates but pose the risk of tumor formation or immune response; whereas adult stem cell technology is easily accessible, but provides limited capacity for transdifferentiation. An optimal approach may be to increase cellular plasticity of adult stem cells for use in autologous transplantation.

BRIEF DESCRIPTION OF THE DRAWINGS

FIG. 5 shows images of Co-culturing experiments which demonstrated that embryoid body-like clusters began differentiation within 48 hours (A). Control cells with our empty vector treatments failed to show any signs of neural differentiation (B). Embryoid-like bodies adhered to membrane and differentiation occurred as neural cells migrated radially outward (C).

FIG. 9 shows sequence of Nanog encoding polynucleotide and corresponding polypeptide sequence (SEQ ID NO: 1 and 2).

FIGS. 10-13 shows gel images of gene expression in cells subjected to various treatments demonstrating an ability to increase potency of mesenchymal stem cells and differentiation into cardiac cells.

DETAILED DESCRIPTION

Figure 1:
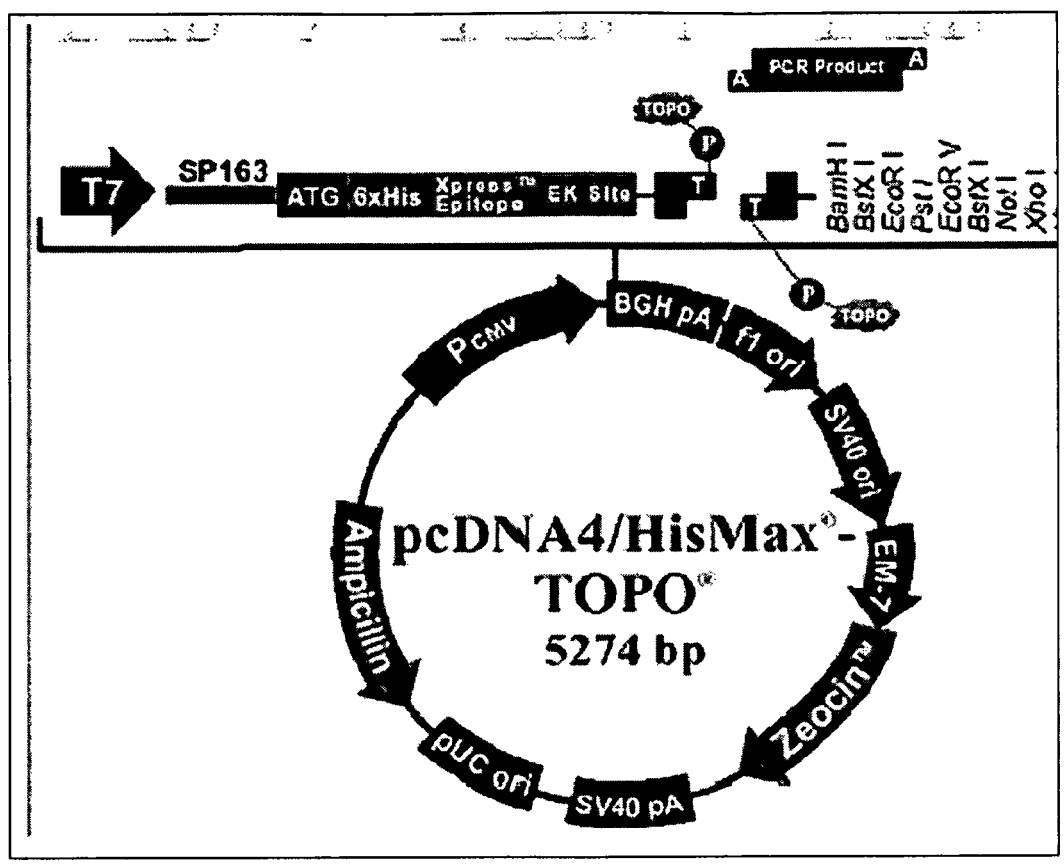
FIG. 1 shows the vector system for cloning nanog according to the teachings in Example 1 (SEQ ID NO: 5).

In reviewing the detailed disclosure which follows, and the specification more generally, it should be borne in mind that all patents, patent applications, patent publications, technical publications, scientific publications, and other references referenced herein are hereby incorporated by reference in this application, in their entirety to the extent not inconsistent with the teachings herein.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

The differentiation of stem cells along multiple lineages has been intensely studied given their great therapeutic potential. However, the mechanisms that underlie proliferation, self-renewal and differentiation in cells with the capacity for further development remains poorly understood. A recently discovered gene, nanog, is required to sustain pluripotency in embryonic stem cells and acts concomitantly with embryonic transcription factor Oct-4, yet utilizes a STAT-3 independent mechanism. The subject invention is based on the inventor's discovery that gene transfection of adult stem cells with nanog, an embryonic stem cell gene maintaining pluripotency [8,9], can allow for the production of neurons and astrocytes from bone marrow cells via a two-step process. First, mesenchymal stem cells are modified by nanog transfection, and the cells form embryoid-like bodies. Then cells are committed to neuronal lineage in a co-culture system with differentiated neural stem cells separated by a semi-permeable membrane. This technology may be a means of generating effective autologous stem cell transplants to improve neuroreplacement strategies. The inventors have discovered that adult stem cells can be dedifferentiated through introduction and expression of the nanog gene or other dedifferentiating genes.

Thus, in one embodiment, the invention provides methods for making a more developmentally potent cell from a less developmentally potent cell. In a typical embodiment, the method comprises the step of introducing an expressible dedifferentiating polynucleotide sequence into a less developmentally potent cell, wherein the transfected less developmentally potent cell becomes a more developmentally potent cell capable of differentiating to a less developmentally potent cell of its lineage of origin or a different lineage. In certain embodiments, the inventive methods further comprise the step of co-culturing the transfected less developmentally potent with neural-lineage cells or media conditioned with neural-lineage cells, wherein the transfected cells become a more developmentally potent cells capable of differentiating to a less developmentally potent cells of its lineage of origin or a different lineage.

In the practice of one embodiment of the invention, the phenotype of the less developmentally potent cell is changed when it becomes a more developmentally potent cell. Thus, the invention provides methods for changing a first phenotype of a less developmentally potent cell into a second phenotype of more developmentally potent cell. The change from a certain potency to a higher level of potency is considered "dedifferentiation" in accord with the teachings herein. In preferred embodiments, the less developmentally potent cell is a stem cell, more preferably a hematopoietic stem cell, a neural stem cell, an epithelial stem cell, an epidermal stem cell, a retinal stem cell, an adipose stem cell and a mesenchymal stem cell.

In yet further aspects of the invention are provided pharmaceutical compositions comprising said more developmentally potent cells prepared according to the methods of the invention and a pharmaceutically-acceptable carrier or excipient. The invention provides such pharmaceutical compositions comprising said more developmentally potent cells that are tissue stem cells for use in cell or tissue regeneration or for correcting a disease or disorder in a tissue or animal in need thereof.

Thus, the invention also provides methods for using the pharmaceutical compositions provided herein to treat an animal in need thereof by administering the more developmentally potent cells thereto. In certain preferred embodiments, the more developmentally potent cells comprise a cluster of two or more of the more developmentally potent cells. Preferably, the animal has a corporal or neurological deficit that can be treated or ameliorated by administration of said more developmentally potent cells, such as a deficit caused by a neurodegenerative disease, a traumatic injury, a neurotoxic injury, ischemia, a developmental disorder, a disorder affecting vision, an injury or disease of the spinal cord, a demyelinating disease, an autoimmune disease, an infection, an inflammatory disease, or corporal disease, disorder, injury, trauma, malfunction, degeneration or loss. In preferred embodiments, the one or plurality of more developmentally potent cells are capable of migrating to an area of tissue damage, differentiating in a tissue-specific manner and functioning in a manner that reduces the neurological or corporal deficit. As provided by the methods of the invention herein, the cells are administered by injecting one or a plurality of more developmentally potent cells with a syringe, inserting the more developmentally potent cells with a catheter or surgically implanting the more developmentally potent cells. In certain embodiments, the more developmentally potent cells are injected with a syringe into a body cavity that is fluidly-connected to the area of neurological or corporal deficit. In certain preferred embodiments, the body cavity is a brain ventricle. In other embodiments, the more developmentally potent cells are inserted with a catheter into a body cavity that is fluidly-connected to the area of neurological or corporal deficit. In certain preferred embodiments, the body cavity is a brain ventricle. In still further additional embodiments, the more developmentally potent cells are surgically implanted into a body cavity that is fluidly-connected to the area of neurological or corporal deficit. In certain preferred embodiments, the body cavity is a brain ventricle. The more developmentally potent cells can also alternatively be inserted using a syringe or catheter or surgically implanted directly at the site of the neurological or corporal deficit or systemically (e.g., intravenously).

Also, the more developmentally potent cells may be further genetically modified through introduction of polynucleotide sequences the bias against differentiation to certain cell types or bias toward differentiation to certain cell types. Provisional Application Nos. 60/621,483 and 60/621,902 naming Dr. Kiminobu Sugaya as an inventor and entitled "Methods and Products For Biasing Development" are incorporated by reference to provide examples of negative and positive biasing that could be subjected to the more developmentally potent cells produced by the methods taught herein.

Administration of the one or a plurality of more developmentally potent cells into an animal results in said cells differentiating into a terminally-differentiated cell. Thus, the invention provides methods for making a terminally-differentiated cell, comprising the step of administering the more developmentally potent cells of the invention into an animal in need thereof. As provided by the methods of the invention herein, the cells are administered by injecting the more developmentally potent cells with a syringe, inserting the more developmentally potent cells with a catheter or surgically implanting the more developmentally potent cells. In certain embodiments, the more developmentally potent cells are injected with a syringe into a body cavity that is fluidly-connected to the area of neurological or corporal deficit. In certain preferred embodiments, the body cavity is a brain ventricle. In other embodiments, the more developmentally potent cells are inserted with a catheter into a body cavity that is fluidly-connected to the area of neurological or corporal deficit. In certain preferred embodiments, the body cavity is a brain ventricle. In still further additional embodiments, the more developmentally potent cells are surgically implanted into a body cavity that is fluidly-connected to the area of neurological or corporal deficit. In certain preferred embodiments, the body cavity is a brain ventricle. The more developmentally potent cells can also alternatively be inserted using a syringe or catheter or surgically implanted directly at the site of the neurological or corporal deficit or systemically (e.g., intravenously).

In yet another embodiment, the invention relates to treating a stem cell, excluding those of neural origin, such that it is converted into a more developmentally potent cell, which enables it to differentiate into the various cell types found in eye tissue, inter alia, chorid, Buchs and retinal pigment epithelium cells, rod and cone photoreceptor cells, horizontal cells, bipolar neurons, amacrine, ganglion and optic nerve cells. These non-limiting, exemplary cell types found in eye tissue are collectively referred to as retinal cells. The methods comprising the step of contacting more developmentally potent cells of the invention with an effective amount of one or a combination of growth factor selected from the group consisting of TGF-b3, IGF-1 and CNTF for an effective period such that the growth factor-contacted cells can differentiate into retinal cells.

As used herein, the terms "multipotent neural stem cells (MNSCs)," "neural stem cells (NSCs)" and "neural progenitor cells (NPCs)" refer to undifferentiated, multipotent cells of the CNS. Such terms are commonly used in the scientific literature. MNSCs can differentiate into tissue-specific cell types, for example astrocytes, oligodendrocytes, and neurons when transplanted in the brain. MNSCs of the invention are distinguished from natural MNSCs by their adaptation for proliferation, migration and differentiation in mammalian host tissue when introduced thereto.

As used herein, a "less developmentally potent cell" is a cell that is capable of limited multi-lineage differentiation or capable of single-lineage, tissue-specific differentiation, for example, an untreated mesenchymal stem cell can differentiate into, inter alia, osteocytes and chondrocytes, i.e., cells of mesenchymal lineage, but has only limited ability to differentiate into cells of other lineages (e.g., neural lineage.).

As used herein, a "more developmentally potent cell" is a cell that is readily capable of differentiating into a greater variety of cell types than its corresponding less developmentally potent cell. For example, a mesenchymal stem cell can readily differentiate into osteocytes and chondrocytes but has only limited ability to differentiate into neural or retinal lineage cells (i.e., it is a less developmentally potent cell in this context). Mesenchymal stem cells treated according to the methods of the invention become more developmentally potent because they can readily differentiate into, for example, mesenchymal-lineage and neural-lineage cell types; the plasticity of the cells is increased when treated according to the methods of the invention.

The invention provides methods of delivery and transplantation of the more developmentally potent cells of the invention to ameliorate the effects of age, physical and biological trauma and degenerative disease on the brain or central nervous system of an animal, as well as other tissues such as, for example, retinal tissue. It is well recognized in the art that transplantation of tissue into the CNS offers the potential for treatment of neurodegenerative disorders and CNS damage due to injury. Transplantation of new cells into the damaged CNS has the potential to repair damaged circuitries and provide neurotransmitters thereby restoring neurological function. It is also recognized in the art that transplantation into other tissue, such as eye tissue, offers the potential for treatment of degenerative disorders and tissue damage due to injury. As disclosed herein, the invention provides methods for generating more developmentally potent cells adapted for proliferation, migration and differentiation in mammalian tissue when introduced thereto. The use of more developmentally potent cells in the treatment of neurological disorders and CNS damage, as well as the use of more developmentally potent cells in the treatment of other tissue damage or degeneration, can be demonstrated by the use of established animal models known in the art.

In one embodiment dedifferentiated cells or more developmentally potent cells of the invention can be administered to an animal with abnormal or degenerative symptoms obtained in any manner, including those obtained as a result of age, physical or biological trauma, or neurodegenerative disease and the like, or animal models created by man using recombinant genetic techniques, such as transgenic and "gene knockout" animals.

Recipients of the more developmentally potent cells of the invention can be immunosuppressed, either through the use of immunosuppressive drugs such as cyclosporin, or through local immunosuppression strategies employing locally applied immunosuppressants, but such immunosuppression need not necessarily be a prerequisite in certain immunoprivileged tissues such as, for example, brain and eye tissues. In certain embodiments, the delivery method of the invention can cause less localized tissue damage to the site of cell damage or malfunction than existing methods of delivery.

More developmentally potent cells of the invention can be prepared from the recipient's own tissue. In such instances, the progeny of the more developmentally potent cells can be generated from dissociated or isolated tissue and proliferated in vitro using the methods described herein. In the case of mesenchymal stem cells (MeSCs), progeny can be generated from MeSCs isolated from, for example, bone marrow. Upon suitable expansion of cell numbers, the stem cells of the invention can be harvested and readied for administration into the recipient's affected tissue.

There are significant differences in the method of delivery to the brain of the more developmentally potent cells compared to the prior art. One exemplary difference is as follows: the more developmentally potent cells of the invention are transplanted intraventricularly. Further, while the transplantation of one or more separate more developmentally potent cells is efficacious, the more developmentally potent cells of the invention are preferably transplanted in the form of clusters of two or more cells via a surgical procedure or injection using a syringe large enough to leave the clusters substantially intact. The results disclosed in the Examples below indicate that ventricular delivery of more developmentally potent cells of the invention in the form of a cluster of two or more cells can result in migration to the area of damage in the brain and proper neuronal differentiation. Another benefit of intraventricular injection is less tissue destruction, resulting in less localized recruitment of immune cells by the host. This is evidenced by the lack of ventricular distortion, tumor formation, and increased host astrocyte staining without any immunosuppression.

The method of delivery of the more developmentally potent cells of the invention to the brain can be essentially duplicated for other immunoprivileged tissue such as, for example, the eye. Delivery of one or more separate or two or more of the more developmentally potent cells in the form of a cluster via injection using a syringe large enough to leave the any cluster of two or more cells that is present substantially intact can result in migration to the area of damage in the eye and proper tissue-specific differentiation.

In the context of the present application, a polynucleotide sequence is "homologous" with the sequence according to the invention if at least 70%, preferably at least 80%, most preferably at least 90% of its base composition and base sequence corresponds to the sequence according to the invention. According to the invention, a "homologous protein" is to be understood to comprise proteins which contain an amino acid sequence at least 70% of which, preferably at least 80% of which, most preferably at least 90% of which, corresponds to the amino acid sequence shown in FIG. 9; wherein corresponds is to be understood to mean that the corresponding amino acids are either identical or are mutually homologous amino acids. The expression "homologous amino acids" denotes those which have corresponding properties, particularly with regard to their charge, hydrophobic character, steric properties, etc. Thus, in one embodiment the protein may be from 70% up to less than 100% homologous to nanog.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48: 443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The term "isolated" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins which contain two or more amino acids which are bound via peptide bonds.

The polypeptides for use in accord with the teachings herein include polypeptides corresponding to nanog, and also includes those, at least 70% of which, preferably at least 80% of which, are homologous with the polypeptide corresponding to nanog, and most preferably those which exhibit a homology of least 90% to 95% with the polypeptide corresponding to nanog and which have dedifferentiating influence. See polypeptide sequence provided in FIG. 9. Thus, the polypeptides may have a homology of from 70% to up to 100% with respect to nanog.

As used herein, a "polypeptide sequence exhibiting dedifferentiating influence" is a polypeptide whose presence in the cell causes an increase in potency, or transformation from a less developmentally potent cell to a more developmentally potent cell. Examples of such polypeptide sequences include the expression products of the nanog gene, and polynucleotide sequences that hybridize to the complement of the sequence in FIG. 9, as well as expression products of the polynucleotide sequences listed in Table 1 below in Example 3.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 600 C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138: 267-284 (1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Accordingly, polynucleotide sequences that hybridize to the complement of the sequence in FIG. 9 are contemplated for use in dedifferentiating cells as taught herein.

U.S. Patent Application Nos. 2003/0219898, 2003/0148513, and 2003/0139410 are incorporated by reference to the extent they are not inconsistent with the teachings herein. These first two of these patent applications describe multiple uses of increased potency cells obtained from the taught methods, and in particular, the implantation of stem cells for different therapeutic treatments of neurological trauma and degenerative conditions. The third patent application is directed to the use of certain compounds to stimulate proliferation and migration of stem cells. Those skilled in the art will readily appreciate that the dedifferentiated cells of the subject invention could be substituted in place of the potent cells taught in the aforementioned patent applications, without undue experimentation. Also, the methods of the third patent may be combined with the present invention without undue experimentation.

According to another embodiment, the subject invention comprises a method of influencing transcription of an endogenous polynucleotide sequence comprising contacting a non-embryonic cell or cellular component comprising an endogenous polynucleotide sequence with a nanog protein or protein encoded by a polynucleotide sequence that hybridizes to a complement of the sequence shown in FIG. 9 under stringent conditions (i.e. nanog-like protein). Such influence may further include, but is not limited to, demethylation of DNA and reversal histone acetylation. The nanog protein or nanog-like protein may be one expressed by a polynucleotide sequence introduced in the cell or cellular component, or protein delivered into the cell or cellular component, or protein expressed by an endogenous polynucleotide sequence that has been activated. Nanog expression may be activated by the provision of Oct 4 and/or Sox2, which typically form a dimer. In a specific embodiment, the cellular component is a nucleus, liposome, or mitochondria. Such endogenous polynucleotide sequence or cellular component contacted by nanog or nanog may be removed from a cell or cellular component and introduced into another cell or cellular component.

In another specific embodiment, the invention pertains to increasing the efficacy of nuclear transfer comprising transfecting a nucleus with a polynucleotide encoding nanog or nanog-like protein to obtain a treated nucleus and introducing the treated nucleus into a cell. The cell may be any suitable cell but would typically be an ovum with its nucleus removed.

EXAMPLE 1

Dedifferentiation of Mesenchymal Stem Cells

Introduction

Embryonic stem cells are derived during the blastocyst stage from the inner cell mass of prenatal mammalia; and possess the intrinsic properties of rapid self-renewal and pluripotency. Under the influence of endogenous and extracellular signals, these cells migrate and differentiate during the developmental process. Extracellular signals regulating self-renewal or differentiation have been demonstrated in vitro by differentiating embryonic stem cells into cell types comprising all three germ layers. These varieties include neuronal, pancreatic, cardiac and hematopoietic tissue using well-established culturing protocols. Embryonic stem cells form embryoid bodies, non-adherent proliferating clusters, in the presence of leukemia-inhibitory factor (LIF) and a feeder layer of typically fibroblast cells. Upon removal of LIF or transfer to non-feeder cell cultures, embryoid bodies undergo spontaneous differentiation. Early differentiation is characterized by loss of stem cell-specific surface antigens (SSEA-1) and alkaline phosphatase activity. Additionally, endogenous signals, including regulatory intracellular proteins, continually change throughout development. Numerous gene expression studies show distinct variations among different embryonic and adult stem cells, pointing toward underlying mechanisms responsible for the continual loss of potency corresponding with differentiation. Several key genes, namely Oct-3/4, LIF, DNMT3B and Nanog, are repeatedly shown to be almost exclusively expressed in embryonic stem cells that regulate pluripotency [10-14]. The immediate down-regulation of these genes may explain irreversible loss of potency, making embryonic stem cells an attractive source for clinical therapies. However, serious questions remain concerning the production of these cells in sufficient quantities for therapies, bioethical potential immune response and tumor formation [15].

The inventors believe that adult stem cells offer a practicable alternative to the use of embryonic tissue as they are easily harvested and potentially taken from autologous sources to preclude immune response. Stem cell populations have been found in several adult tissues including adipose [16], muscle [17], pancrease [18] and liver [19] and primarily bone marrow [20-23]; all potential sources for cellular transplants [24]. Previous in vitro studies with adult bone marrow-derived stem cells have demonstrated the ability to differentiate into brain [21], liver [23] and cardiac cells [22]. In vivo studies have shown evidence that adult stem cells can migrate and differentiate into various tissues, albeit at extremely low frequencies [20]. However, challenges have been raised over the plasticity of these cells given both the low frequencies of detected cells and new found evidence of cell fusion, in conjunction with false positives [25-27]. An ideal therapeutic alternative may exist if adult cells can be dedifferentiated to an embryonic-like state and recommitted to differentiate to a desired cell fate.

Nanog, also referred to as early embryo specific NK (ENK) [28], is a recently discovered gene responsible for maintaining pluripotency in embryonic stem cells [8,9,28,29]. This unique gene and its cousin, Nanog2, are genetically distinct members of the ANTP class of homeodomain proteins [30] and have at least twelve identified pseudogenes [31]. Structurally, Nanog contains three alpha helixes encoded within the homeodomain portion and can be divided into three regions with respect to the central homeodomain sequence [30]. The N-terminal region is rich in serine and threonine residues indicating phosphate-regulated transactivation, possibly through SMAD4 interactions, while the C-terminal domain is seven times as active with an unusual motif of equally spaced tryptophans separated by four amino acids, each flanked with serine or threonine residues. Gene expression studies have shown nanog to be active in embryonic stem cells, tumors and some adult tissue. Nanog expression precipitously decreases with differentiation and maintains self-renewal in embryonic stem cells by gene transfection. In culture, nanog guards against differentiation and acts concomitantly with Oct-4, Wnt and BMP-4, yet utilizes a STAT-3 independent mechanism to maintain an undifferentiated state. Inventors believe that the role of nanog in regulating pluripotency makes this gene a potential candidate for increasing the potency of adult stem cells.

Previous studies regulating gene expression in stem cell lines have provided valuable insight into underlying mechanisms of proliferation, self-renewal and differentiation. Gene manipulation experiments can either prevent or enhance differentiation. In particular, differentiation can be prevented in embryonic stem cell lines by over expression of Pem or nanog, genes that regulate pluripotency. Conversely, overexpression of lineage specific gene Nurr1 promotes the differentiation of neura 1 stem cell lines to produce dopamine-secreating cells. Taken together, gene vectors can maintain cells in a specific state or allow for lineage committed cells to develop into a specific subpopulation. In one embodiment, the subject invention pertains to a method of dedifferentiating adult stem cells by expressing genes regulating pluripotency to enhance transdifferentiation. This technology allows for adult cells to be used for autologous transplantation and thereby provide a greater understanding of stem cell biology.

Figure 17:
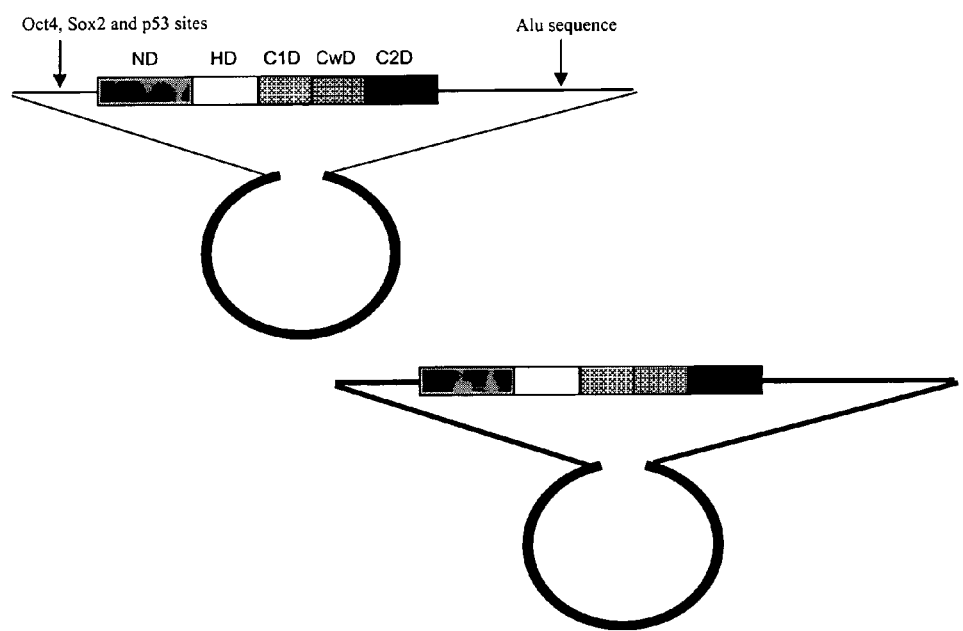
FIG. 17 shows a schematic representation of the nanog sequence cloned inside a CMV mammalian promoter vector.

FIG. 17 shows a schematic representation of the nanog sequence cloned inside a CMV mammalian promoter vector. The 5'UTR contains an Oct-4 and Sox2 binding region. The nanog protein coding sequence can be divided into an N-terminal, homeodomain and C-terminal region. The C-terminal region can be further subdivided into a C1, Cw and C2 domains. The 3' UTR contains an Alu sequence element.

Methods and Results

Human mesenchymal stem cells (hMeSC) are initially plated in 6-well plates, adhere to the surface and allowed to divide to varying degrees of confluence. They are cultured in serum-DMEM (Dulbecco's modified Eagle's medium) containing 10% FCS, 5% HS, 292 mg/ml glutamine, 50 U/ml streptomycin and penicillin (all from Invitrogen).

Cloning of nanog was achieved by first performing polymerase chain reaction with primers corresponding to the nanog gene family (5'-tttttcctcctcttcctcta-3' and 5'-attggtgat-gaagatgtatt-3') against a human genome DNA template. The PCR product was cloned into pcDNA Hismax TOPO® TA cloning mammalian expression vector (Invitrogen) and inserted in E. coli. See FIG. 1. Bacterial cells were plated on agar plates containing LB agar and ampacillin and incubated overnight at 37° C. Isolated colonies were transferred to growth media and grown overnight in a 37° C. rotating at 200 rpm. Plasmid isolation was performed using endotoxin free maxiprep (Beckon Dickenson) or miniprep kits (Clonetech). Gene segment was then confirmed by gel electrophoresis through enzyme digestion and DNA sequencing. The gene product was approximately 1600 base pairs, consistent with the nanog gene. However, sequencing analysis matched nanog pseudogene 8 (NANOG8), a segment containing no introns and sharing 99 percent homology with nanog. See . The deduced protein product is almost identical with two differing amino acids. The gene product encodes for a nanog-like protein with a 305 amino acid serine/threonine-rich sequence. The protein can be divided into three distinct domains at the N-terminal, homeodomain and C-terminal as previously described.

Upon reaching a desired cell number, approximately 75% confluence, HMeSCs were transfected with above-mentioned vector using NeuroPorter (Gene Therapy System) transfection system. Concentrations of NeuroPorter and DNA (0.5 µg/ml to 40 µg/ml) were varied to achieve optimal results. Cells became non-adherent and began to multiply, forming spherical clusters: consistent with embryoid body formation. Thus, they achieved characteristics of embryonic stem cells.

Figure 2:
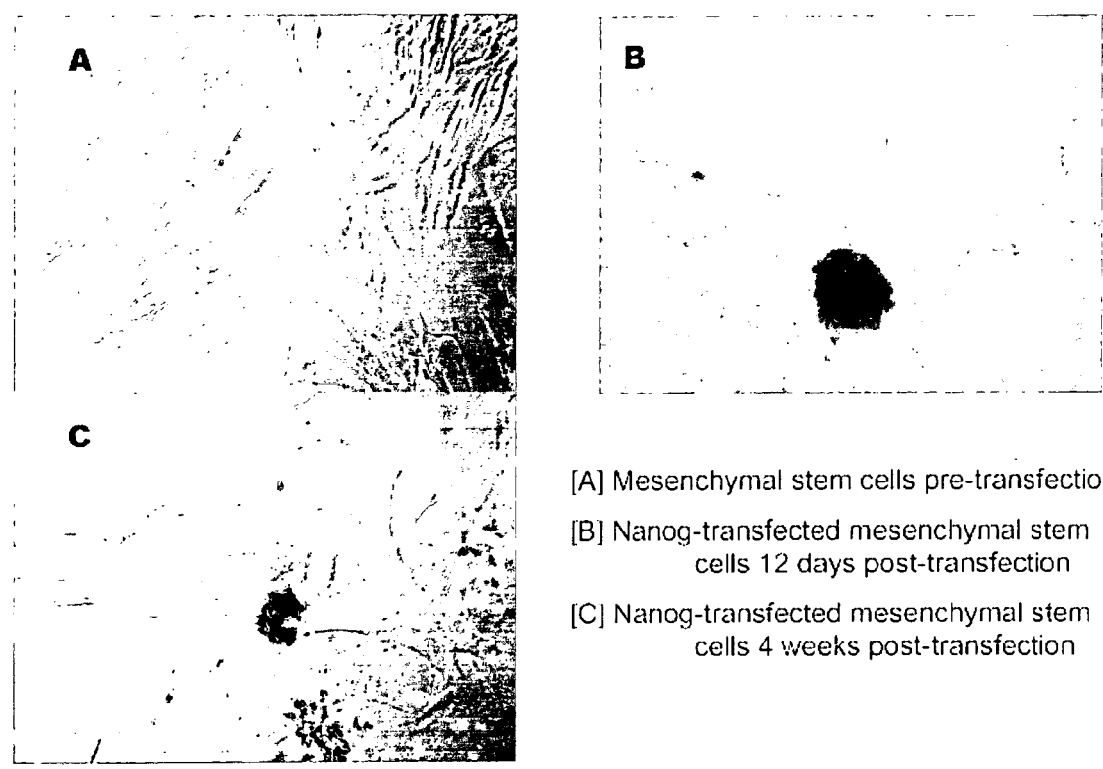
FIG. 2 shows images of cells before and after transfection with nanog: A: shows mesenchymal stem cells pre-transfection; B: shows nanog-transfected mesenchymal stem cells 12 days post-cells 12 days post-transfection; C: shows nanog-transfected mesenchymal stem cells 4 weeks post-cells 4 weeks post-transfection.
Figure 3:
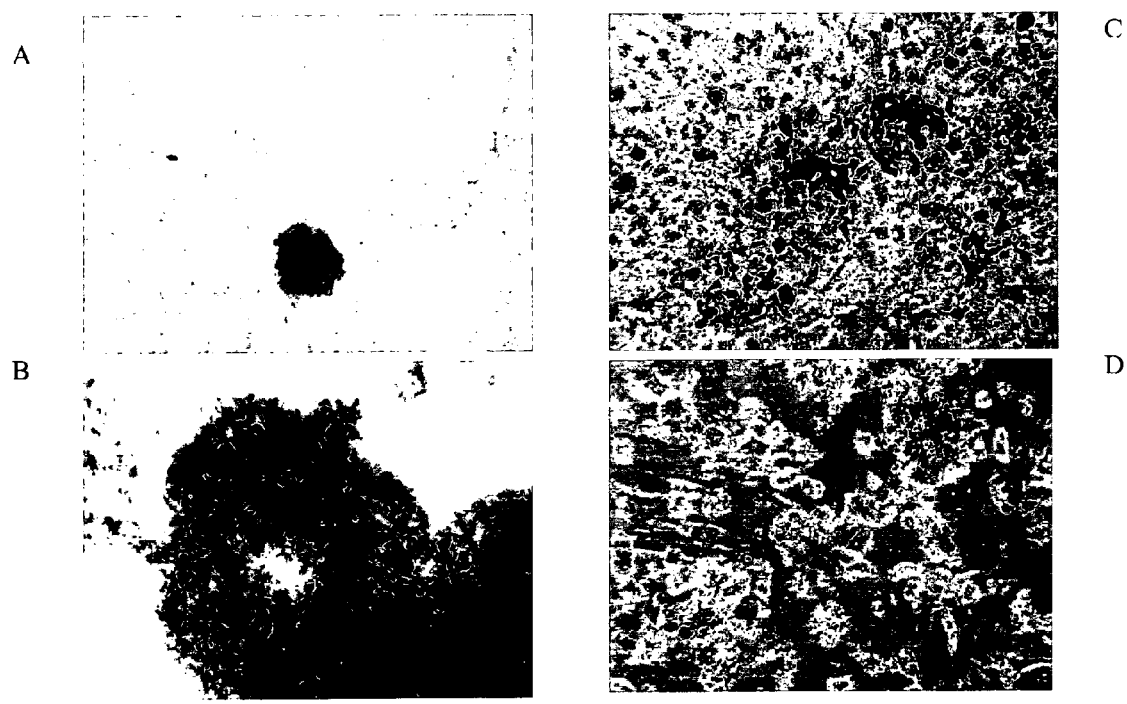
FIG. 3 shows images of transfected mesenchymal stem cells 9 days (A and B) and 2 months (C and D) post transfection.
Figure 4:
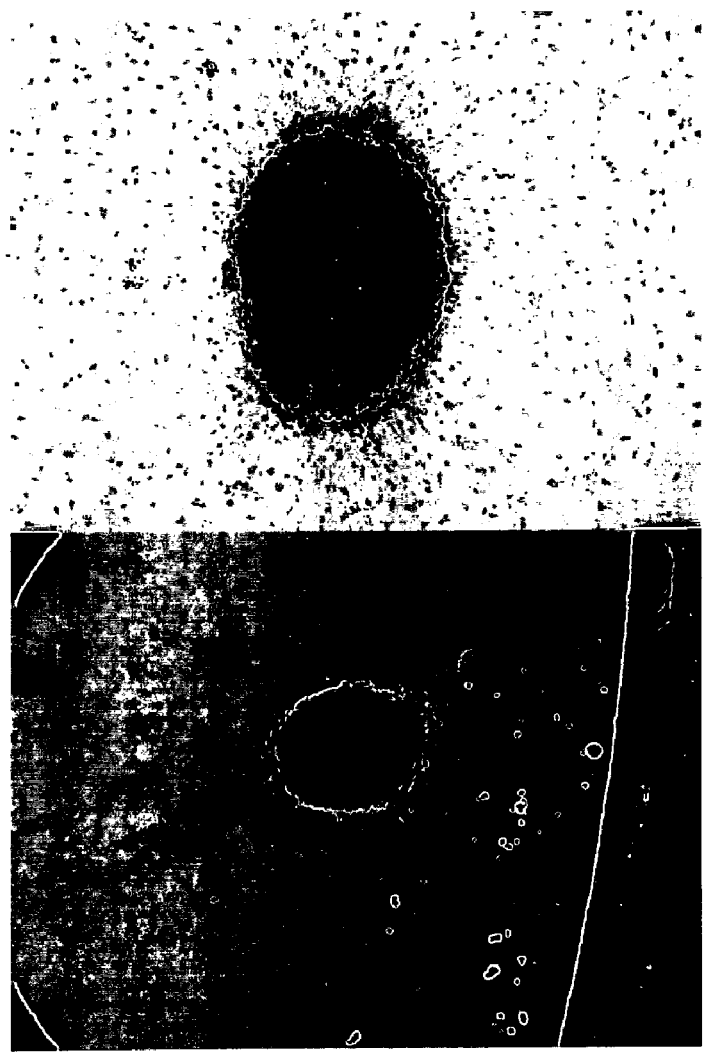
FIG. 4 shows images a co-culture system in accord with one embodiment of the subject invention.

Nanog transfection of mesenchymal stem cells resulted in morphological changes similar to embryoid body formation (FIG. 2-4). Cellular transformation occurred in a pattern of transfection, non-adherence, survival and proliferation. Non-adherent clusters proliferated in vitro beyond two months in the presence of remaining adherent mesenchymal stem cells.

To determine if nanog could restore pluripotency in adult cells rather than simply maintain the state in embryonic cells, the inventors developed a two-step process of dedifferentiation and development along an alternative lineage, discussed in Example 2 below. Human mesenchymal stem cells were cultured in a six-well culture plates and were allowed to adhere and grow for at least 48 hours to achieve approximately 75% confluence. Cells were subsequently transfected with a mammalian cell vector or control vehicle, cultured and examined. Cells transfected with NANOGP8 became non-adherent and proliferated in the presence of the remaining adherent cells acting as a feeder layer. Control samples receiving empty transfection did not show any proliferation and decreased dramatically, likely due to the toxicity of the transfection. Transferring non-adherent cells to wells without a feeder layer resulted in apoptosis, related to either absence of feeder cell proteins of decreased cell density. Cellular transformation occurred in a pattern of transfection, non-adherence, survival and proliferation. Transformed cells proliferated in three-dimensional clusters for months in culture. These characteristics are similar to embryonic stem cells.

EXAMPLE 2

Neuronal Differentiation of Dedifferentiated Mesenchymal Cells

Figure 6:
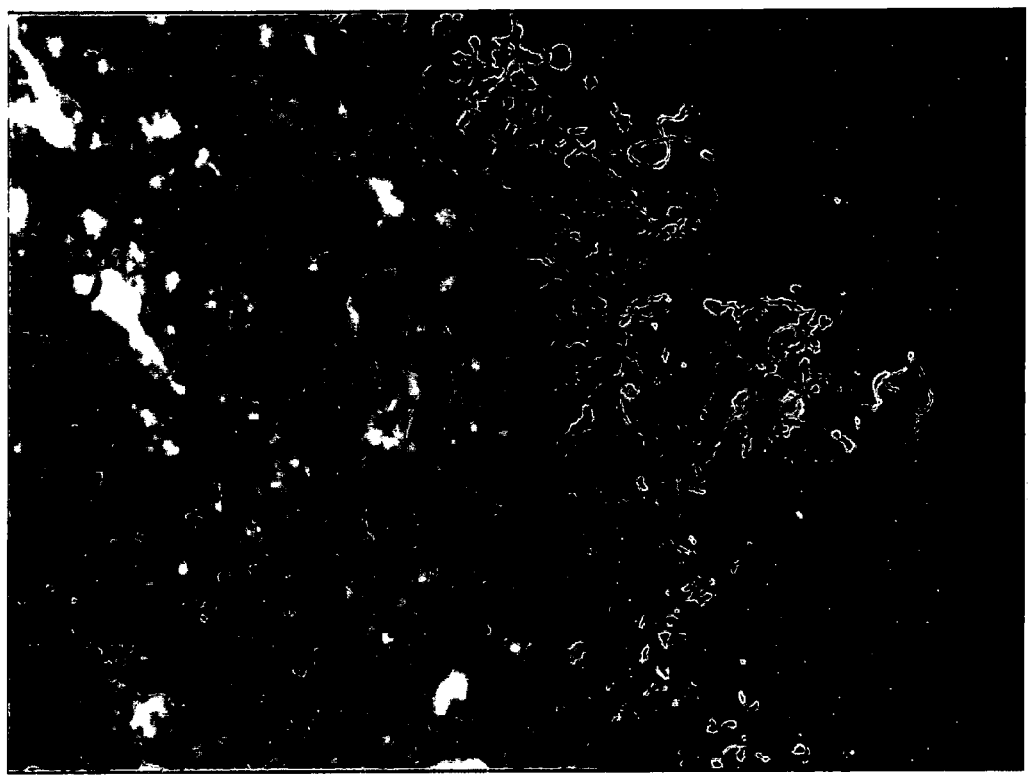
FIG. 6-7 show images of the clustering of nanog transfected cells.

To test whether cells can be dedifferentiated using nanog and committed to an alternate lineage we utilized a co-culture system of differentiated human neural stem cells and transformed mesenchymal cells. Neural stem cells spheres were placed in 12 well plates and differentiated using serum-free basal media as previously described. Neuronal stem cells began to differentiate by becoming adherent and migrating radially outwards from the original neural sphere. Following neural stem cell differentiation, these cells were utilized as feeder cells in our co-culture system by placing modified cells inside co-culture chamber that separated modified stem cells from the feeder layer with a 0.2 µm semipermeable membrane. See FIG. 5. Within 48 hours, transferred cells began to display characteristics of differentiation marked by morphological alterations, membrane adherence and outward migration. FIG. 6. Immunohistochemical analysis revealed positive markers for β-III tubulin and GFAP, showing neuron and glial differentiation. Positive staining for mixed neuronal populations was observed in non-adherent clusters cultured for more than 48 hours, adherent cell masses and individual membrane bound cells.

Figure 7:
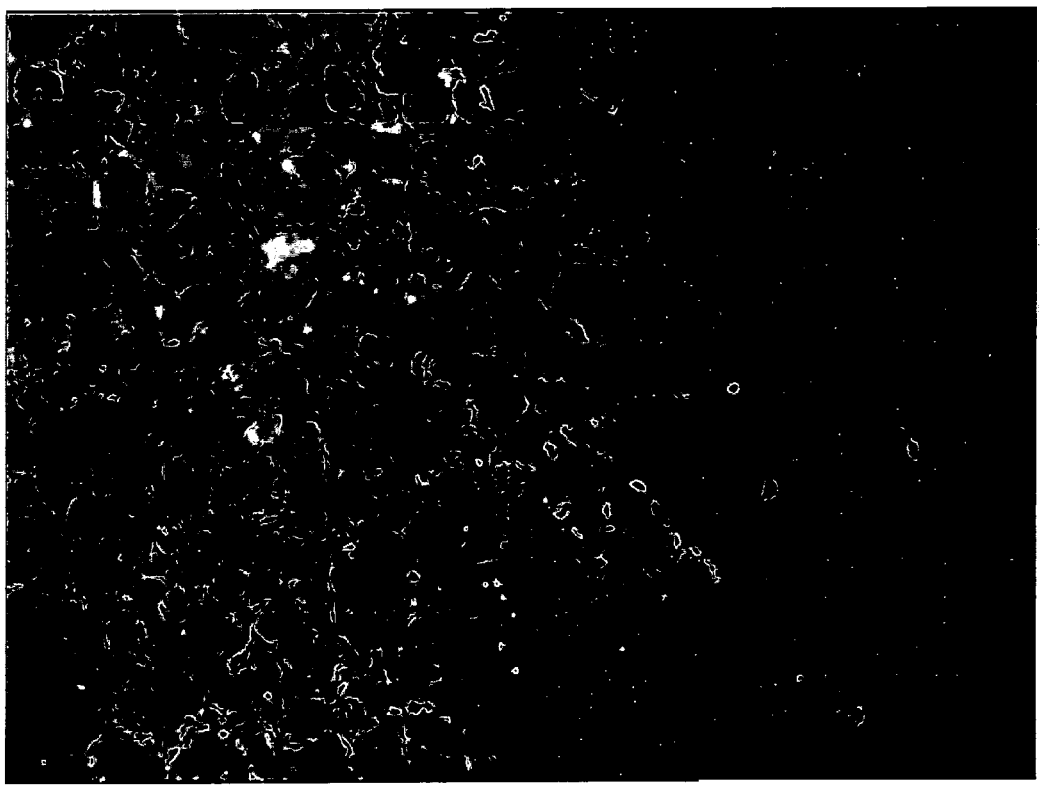
Figure 8:
FIG. 8 shows images of MeSC-derived neurons and astrocytes.

Co-culturing experiments showed embryoid body-like clusters began differentiation within 48 hours. Control cells with our vector treatments failed to show any signs of neural differentiation. Immunohistochemical staining revealed nanog transfected samples intensely stained positive for βIII-tubulin and GFAP, indicating neuron and astrocyte differentiation. See FIGS. 6-7. Originally, nanog-transformed cells remain in a cluster of differentiating neural cells that continually radiate outward (See FIGS. 6-7). FIG. 8 shows MeSC derived neurons and astrocytes.

EXAMPLE 3

Dedifferentiation of Cells Utilizing Genes Affecting Pluripotency

Following the transfection and evaluation protocol provided above in Example 1, PCR products of the genes in Table 1 are evaluated for their ability to dedifferentiate cells, particularly mesenchymal stem cells.

TABLE 1

Pem (mouse GI:1255173)
Fan Y, et al. Developmental Biology 210: 481-496. 1999
POU5F1 (Unigene Hs.2860)
Sox2 (Unigene Hs.816)
HESX1 (Unigene Hs.171980)
UTF1 (Unigene Hs.158307)
REX1 (Unigene Hs.335787)
FOXD3 (Unigene Hs.120204)
GBX2 (Unigene Hs.326290)
NANOG (Unigene Hs.326290)
LIN-28 (Unigene 86154)
TGIF
DNMT3A/B (251673)
TGFF1 (75561)
Richards M, et al. Stem Cells 22: 51-64. 2004
EGS-1 (accession # X57708.1)
FGF4 Tanaka T, et al. Genone Research 12: 1921-1928. 2002.
Rex-1 (accession#AF450454)

NUMBERED REFERENCES

1. Sugaya K. Potential use of stem cells in neuroreplacement therapies for neurodegenerative diseases. Int Rev Cytol. 2003; 228: 1-30.
2. Armstrong R J, Harrower T P, Hurelbrink C B, McLaughin M, Ratcliffe E L, Tyers P, Richards A, Dunnett S B, Rosser A E, Barker R A. Porcine neural xenografts in the immunocompetent rat: immune response following grafting of expanded neural precursor cells. Neuroscience. 2001; 106 (1): 201-16.
3. Trojanowski J Q, Kleppner S R, Hartley R S, Miyazono M, Fraser N W, Kesari S, Lee V M. Transfectable and transplantable postmitotic human neurons: a potential "platform" for gene therapy of nervous system diseases. *Exp Neurol.* 1997; 144(1): 92-7.
4. Zlokovic B V, Apuzzo M L. Cellular and molecular neurosurgery: pathways from concept to reality—part I: target disorders and concept approaches to gene therapy of the central nervous system. Neurosurgery. April 1997; 40(4): 789-804
5. Qu T Y, Dong X J, Sugaya I, Vaghani A, Pulido J, Sugaya K. Bromodeoxyuridine increases multipotency of human bone marrow-derived stem cells. (in press).
6. Chang G, Sugaya K. Inner ear hair cell generation from human neural stem cells through Math1 transfection. Program No. 303.1. 2004 Abstract Viewer/Itinerary Planner. Washington, D.C.: Society for Neuroscience, 2004.
7. Wagner J, Akerud P, Castro D S, Holm P C, Canals J M, Snyder E Y, Perlmann T, Arenas E. Induction of a midbrain dopaminergic phenotype in Nurr1-overexpressing neural stem cells by type 1 astrocytes. Nat Biotechnol. July 1999; 17(7): 653-9.
8. Chambers I, Colby D, Robertson M, Nichols J, Lee S, Tweedie S, Smith A. Functional expression cloning of Nanog, a pluripotency sustaining factor in embryonic stem cells. *Cell.* 2003; 113(5): 643-55.
9. Mitsui K, Tokuzawa Y, Itoh H, Segawa K, Murakami M, Takahashi K, Maruyama M, Maeda M, Yamanaka S. The homeoprotein Nanog is required for maintenance of pluripotency in mouse epiblast and ES cells. *Cell.* 2003; 113(5): 631-42.
10. Bhattacharya B, Miura T, Brandenberger R, Majido J, Luo Y, Yang A X, Joshi B H, Ginis I, Thies R S, Amit M, Lyons I, Condie B G, Itskovitz-Eldor J, Rao M S, Puri R K. Gene expression in human embryonic stem cell lines: Unique molecular signature. *Blood.* 2004; 103(8): 2956-2964.
11. Calhoun J D, Rao R R, Warrenfeltz S, Rekaya R, Dalton S, McDonald J, Stice S L. Transcriptional profiling of initial differentiation events in human embryonic stem cells. Biochem Biophys Res Commun. Oct. 15, 2004; 323 (2): 453-64.
12. Clark A T, Rodriguez R T, Bodnar M S, Abeyta M J, Cedars M I, Turek P J, Firpo M T, Reijo Pera R A. Human STELLAR, NANOG, and GDF3 genes are expressed in pluripotent cells and map to chromosome 12p13, a hotspot for teratocarcinoma. *Stem Cells.* 2004; 22(2): 169-179.
13. Spencer J M, Chen X, Draper J S, Antosiewicz J E, Chon C H, Jones S B, Brooks J D, Andews P W, Brown P O, Thomson J A. Gene expression patterns in human embryonic stem cells and human pluripotent germ cell tumors. Proc Nat Acad Sci USA. 2003; 100(23): 13350-13355.
14. Tanaka T S, Kunath T, Kimber W L. Jaradat S A, Stagg C A, Usada M, Yokota T, Niwa H, Rossant J, Ko M. Gene expression profiling of emryo-derived stem cells reveals candidate genes associated with pluripotency and lineage specificity. Genome Res. 2002; 12: 1921-1928.
15. Erdo F, Buhrle C, Blunk J, Hoehn M, Xia Y, Fleischmann B, Focking M, Kustermann E, Kolossov E, Hescheler J, Hossmann K A, Trapp T. Host-dependent tumorigenesis of embryonic stem cell transplantation in experimental stroke. J Cereb Blood Flow Metab. July 2003; 23(7): 780-5.
16. Gimble J, Guilak F. Adipose-derived adult stem cells: isolation, characterization, and differentiation potential. Cytotherapy. 2003 ; 5(5): 362-9.
17. Cao B, Huard J. Muscle-derived stem cells. Cell Cycle. February 2004; 3(2): 104-7.
18. Hess D, Li L, Martin M, Sakano S, Hill D, Strutt B, Thyssen S, Gray D A, Bhatia M. Bone marrow-derived stem cells initiate pancreatic regeneration. Nat Biotechnol. July 2003; 21(7): 763-70.
19. Muller-Borer B J, Cascio W E, Anderson P A, Snowwaert J N, Frye J R, Desai N, Esch G L, Brackham J A, Bagnell C R, Coleman W B, Grisham J W, Malouf N N. Adult-derived liver stem cells acquire a cardiomyocyte structural and functional phenotype ex vivo. Am J Pathol. July 2004; 165(1): 135-45.
20. Jiang Y, Jahagirdar B N, Reinhardt R L, Schwartz R E, Keene C D, Ortiz-Gonzalez X R, Reyes M, Lenvik T, Lund T, Blackstad M, Du J, Aldrich S, Lisberg A, Low W C, Largaespada D A, Verfaillie C M. Pluripotency of mesenchymal stem cells derived from adult marrow. Nature. Jul. 4, 2002; 418(6893): 41-9.
21. Brazelton T R, Rossi F M, Keshet G I, Blau H M. From marrow to brain: expression of neuronal phenotypes in adult mice. *Science. Dec.* 1, 2000; 290(5497): 1775-9.
22. Fukuda K. Use of adult marrow mesenchymal stem cells for regeneration of cardiomyocytes. Bone Marrow Transplant. August 2003; 32 Suppl 1: S25-7.
23. Theise N D, Nimmakayalu M, Gardner R, Illei P B, Morgan G, Teperman L, Henegariu O, Krause D S. Liver from bone marrow in humans. Hepatology. July 2000; 32(1): 11-6.
24. Hedrick M H, Daniels E J. The use of adult stem cells in regenerative medicine. Clin Plast Surg. October 2003; 30(4): 499-505.
25. Alvarez-Dolado M, Pardal R, Garcia-Verdugo J M, Fike J R, Lee H O, Pfeffer K, Lois C, Morrison S J, Alvarez-Buylla A. Fusion of bone-marrow-derived cells with Purkinje neurons, cardiomyocytes and hepatocytes. Nature. Oct. 30, 2003; 425(6961): 968-73
26. Terada N, Hamazaki T, Oka M, Hoki M, Mastalerz D M, Nakano Y, Meyer E M, Morel L, Petersen B E, Scott E W. Bone marrow cells adopt the phenotype of other cells by spontaneous cell fusion. Nature. Apr. 4, 2002; 416(6880): 542-5.
27. Wu T, Cieply K, Nalesnik M A, Randhawa P S, Sonzogni A, Bellamy C, Abu-Elmagd K, Michalopolous G K, Jaffe R, Kormos R L, Gridelli B, Fung J J, Demetris A J. Minimal evidence of transdifferentiation from recipient bone marrow to parenchymal cells in regenerating and long-surviving human allografts. Am J Transplant. September 2003; 3(9): 1173-81.
28. Wang S, Tsai M, Chiang M, Li H. A novel NK-type homeobox gene, ENK (early embryo specific NK), preferentially expressed in embryonic stem cells. *Gene Exp Patterns* 2003; 3: 99-103.
29. Hart A H, Hartley L, Ibrahim M, Robb L. Identification, cloning and expression analysis of the pluripotency promoting Nanog genes in mouse and human. *Dev Dyn.* 2004; 230(1): 187-198.
30. Pan G J, Pei D Q. Identification of two distinct transactivation domains in the pluripotency sustaining factor nanog. *Cell Res.* 13 (6): 499-502.
31. Booth H A, Holland P W. Eleven daughters of NANOG. *Genomics.* 2004; 84(2): 229-238.

EXAMPLE 4

Cardiac Differentiation of Human Mesenchymal Cells

Cardiac differentiation of human mesenchymal stem cells (MeSCs) is achieved through treatment with nucleotide derivatives BrdU and 5-azaC and/or forced expression of embryonic stem cell gene nanog. Following treatment, cells were placed in a co-culture with cardiac cells (cardiomyocyte cell line H9c2). Human MeSCs plated in 6-well culture plates and expanded in serum-DMEM (Delbecco's Modified Eagle's Medium) containing 10% MeSC formulated fetal bovine serum (FBS, Stem Cell, Inc) containing antibiotics/ antimycotics. MeSCs were treated with varying concentrations (1-10 uM) of BrdU and/or 5-azaC for 3 weeks or transfected with mammalian expression vector containing a nanog encoding sequence. Cell media was changed every three days prior to co-culture with cardiomyocytes. Cardiomyocytes were expanded and grown to near confluence in serum-DMEM with 10% non-conditioned FBS and antibiotics/antimycotics. To differentiate cardiac cells, serum media was replaced with plain DMEM containing only antibiotics and allowed to differentiate. Co-cultures were created by combining MeSCs with cardiac cells and culturing in cardiac media. Following co-culture, cells were treated with TRIzol and gene expression was assessed using RT-PCR and cardiac specific primers. Gel electrophoresis of samples revealed expression of cardiac specific genes following treatment.

Figure 10:
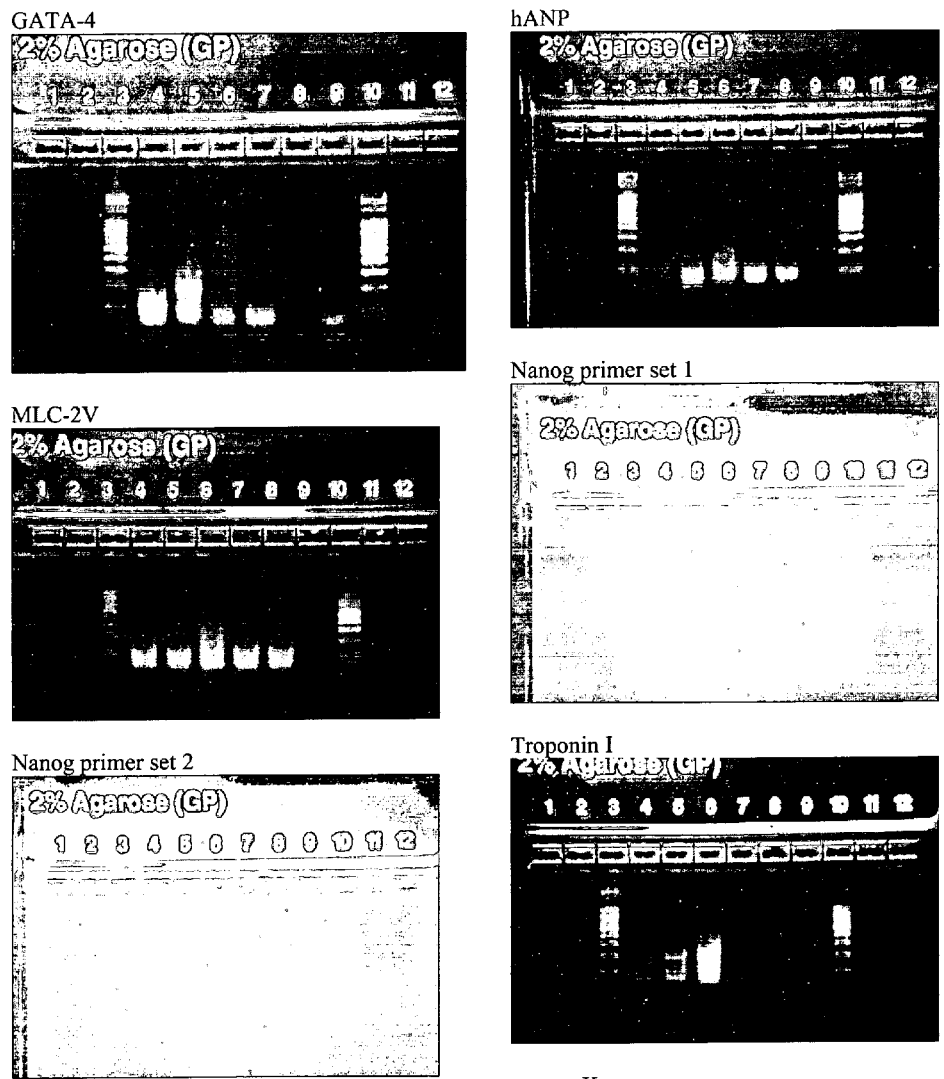
Figure 14:
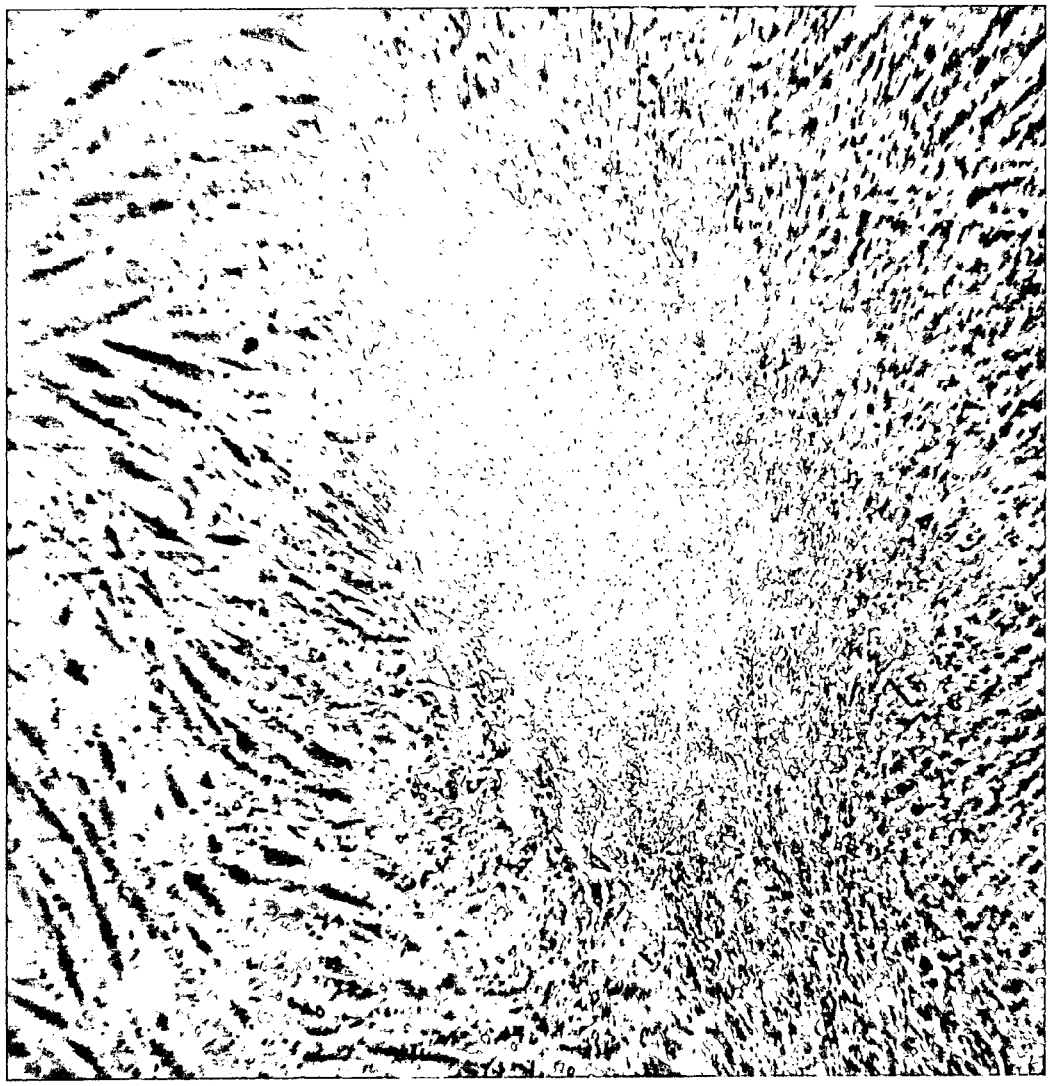
FIGS. 14-16 show photograph images of cells subjected to various treatments.
Figure 15:
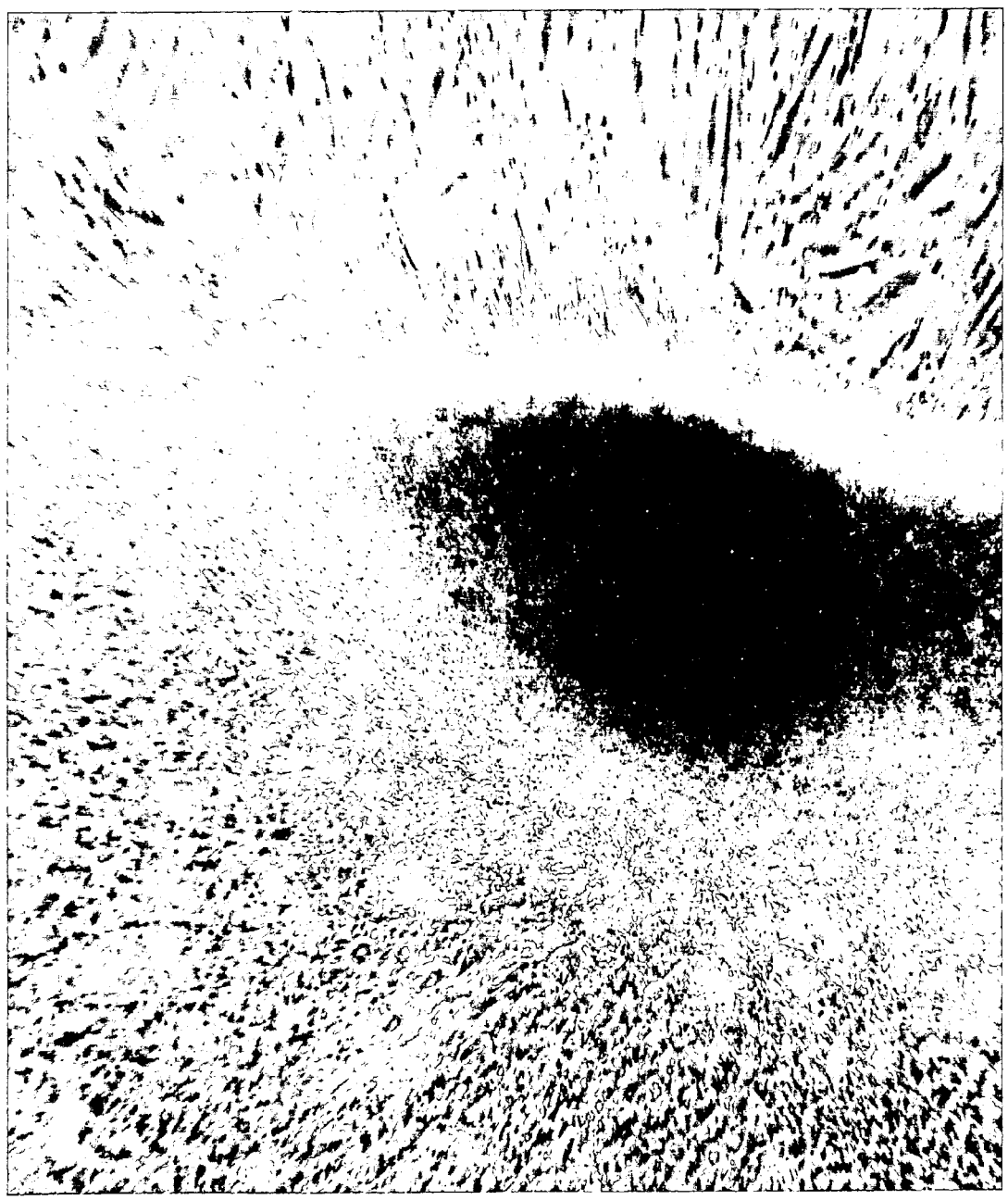
Figure 16:

The first (Electrophoresis 050101, FIG. 10) shows screens for each primer tested. The key shows which sample is in a given lane. Negative control represents untreated mesenchymal stem cells and Positive controls 1× and 2× are nanog transfected MeSCs (2× indicates that well received twice the number of rat cardiac cells, not twice the amount of nanog transfected cells). Each sample was co-cultured with rat cardiomyocytes and primers are human specific and represent markers of cardiomyocyte related gene expression. The second data set (Electrophoresis 050115, FIG. 11) shows gene expression for each primer following 3 uM treatment of either BrdU or 5azaC. The high and low RNA is because we had low cell numbers and tested one well (low RNA) against combining two wells of equal treatment (high RNA). The third attachment (Electrophoresis 050116, FIG. 12) shows the effects of three weeks treatment of combined (3 uM or 1 uM of both 5azaC and BrdU), 3 uM of either 5azaC or BrdU, or nanog transfected cells (marked "control"). The poor quality is the result of low cell numbers and the use of a different RT-PCR kit (BioRad instead of the usual Invitrogen). See also FIG. 13. FIGS. 14-16 pertain to photograph images of MeSCs treated with 3 uM of 5azaC (A 050123 3 uM 5azaC 3weeks MSCjpg, FIG. 14), of 3 uM of BrdU (A 050123 3 uM BrdU 3weeks MSCjpg, FIG. 15) and of nanog transfected cells combined with rat cardiac cells in co-culture (A 41227 of ntMSC 1213 2.jpg, FIG. 16). The cell differentiation is due to environmental signals and cell to cell contacts.

The inventors demonstrate that treatment with nucleotide derivatives and/or nanog transfection provides for cardiac differentiation of mesenchymal stem cells. Accordingly, an embodiment of the invention pertains to a method of increasing the potency of a cell comprising introducing a gene comprising nanog activity, optionally in conjunction with treatment of such cell with a compound, such as a nucleotide derivative, known to exert a dedifferentiating influence on cells.

What is claimed is:

1. A method of increasing the developmental potency of an adult mesenchymal stem cell comprising introducing into said adult mesenchymal stem cell a nanog gene, and culturing said adult mesenchymal stem cell under conditions to allow expression of said nanog gene, wherein said expression results in higher developmental potency of said adult mesenchymal stem cell.

2. A method of creasing developmental potency of a mesenchymal stem cell comprising introducing into said cell a nanog gene under conditions to allow expression of said polynucleotide, wherein said expression results in higher developmental potency of said cell.

3. A method of transforming an adult mesenchymal stem cell into a pluripotent cell comprising (a) introducing into said adult mesenchymal stem cell a nanog gene; and (b) culturing the adult mesenchymal stem cell from step (a) in a tissue culture environment to allow time to express the protein, thereby causing dedifferentiation of said adult mesenchymal stem cell into a pluripotent state.

4. A method of differentiating a dedifferentiated adult mesenchymal stem cell, the method comprising exposing the dedifferentiated adult mesenchymal stem cell from claim 3 to differentiating factors influencing differentiation into a neural cell type.

5. A method of producing an autologous dedifferentiated cell sample comprising obtaining a sample of adult mesenchymal stem cells from a subject; introducing a nanog gene into said adult mesenchymal stem cells, thereby transforming said adult mesenchymal stem cells; and culturing said transfected adult mesenchymal stem cells in a tissue culture environment to allow time to express the nanog gene, thereby causing dedifferentiation of said transfected cells.

* * * * *